(12) United States Patent
Nakamura

(10) Patent No.: US 6,473,682 B2
(45) Date of Patent: Oct. 29, 2002

(54) APPARATUS AND METHOD FOR ESTIMATING MAXIMUM ROAD FRICTION COEFFICIENT

(75) Inventor: Akira Nakamura, Tagata-gun (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/987,140

(22) Filed: Nov. 13, 2001

(65) Prior Publication Data

US 2002/0111752 A1 Aug. 15, 2002

(30) Foreign Application Priority Data

Nov. 20, 2000 (JP) .......................................... 2000-353446

(51) Int. Cl.[7] .............................. G01N 3/56; G06F 7/00; G06F 17/00; G06F 19/00
(52) U.S. Cl. ............................. 701/74; 701/71; 701/80; 73/9; 73/10; 180/197; 152/454; 152/525; 152/538; 152/209.2; 303/150
(58) Field of Search ............................... 701/74, 80, 71; 180/197; 73/9, 10; 152/454, 525, 538, 209.2, 209.18; 303/150

(56) References Cited

U.S. PATENT DOCUMENTS

| | | | | |
|---|---|---|---|---|
| 5,948,961 A | * | 9/1999 | Asano et al. ..................... 73/9 |
| 6,089,680 A | * | 7/2000 | Yoshioka et al. ............ 303/140 |
| 6,102,093 A | * | 8/2000 | Nakagawa ............. 152/209.18 |
| 6,122,585 A | * | 9/2000 | Ono et al. .................... 180/197 |
| 6,266,601 B1 | * | 7/2001 | Soga et al. ................... 180/197 |
| 6,308,126 B2 | * | 10/2001 | Yokoyama et al. ......... 180/197 |
| 2001/0007965 A1 | * | 7/2001 | Yokoyama et al. ............ 701/70 |

FOREIGN PATENT DOCUMENTS

JP    A 3-295445    12/1991

* cited by examiner

*Primary Examiner*—William A. Cuchlinski, Jr.
*Assistant Examiner*—Ronnie Mancho
(74) *Attorney, Agent, or Firm*—Oliff & Berridge, PLC

(57) ABSTRACT

An apparatus and method that determines a maximum road friction coefficient for each wheel regardless of whether the tire is in a predetermined drive slip state, and whether the wheel is a driving wheel. The braking force of each wheel is calculated, and the longitudinal force of the tire of each wheel is calculated. Then, the driving force of the vehicle is calculated, and the lateral force of the tire of each wheel is calculated. Next, the reaction force of the road to each wheel is calculated, and the vertical load of each wheel is calculated. Finally, the ratio of variation in reaction force of the road to variation in composite slip ratio is calculated for each wheel. The sum of the ratio of the reaction force of the road to the vertical load, and the product of a predetermined coefficient and the ratio of variation in reaction force of the road to variation in composite slip ratios is calculated for each wheel as the maximum road friction coefficient.

19 Claims, 10 Drawing Sheets

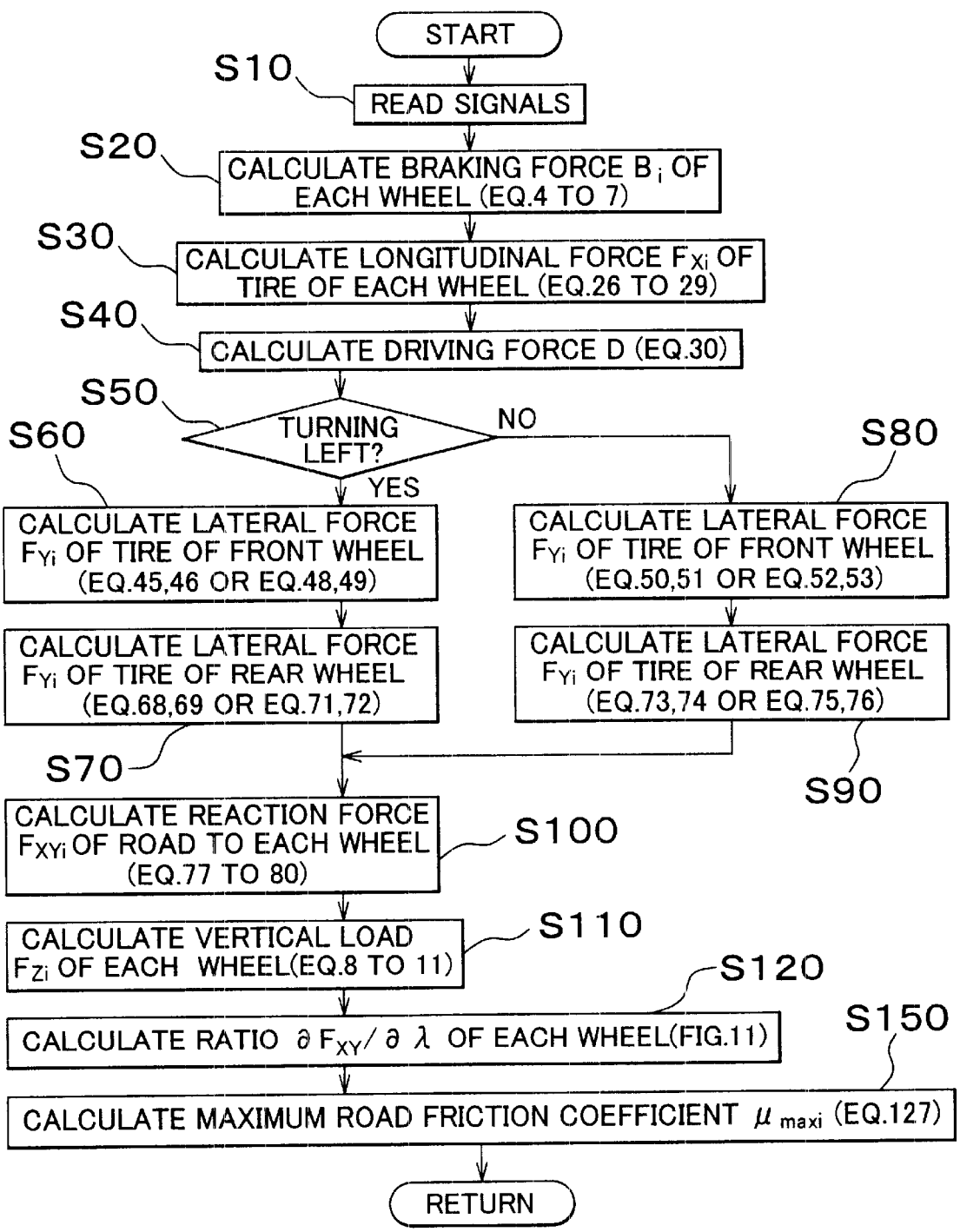

US 6,473,682 B2

1

APPARATUS AND METHOD FOR ESTIMATING MAXIMUM ROAD FRICTION COEFFICIENT

INCORPORATION BY REFERENCE

The disclosure of Japanese Patent Application No. 2000-353446 filed on Nov. 20, 2000 including the specification, drawings and abstract is incorporated herein by reference in its entirety.

BACKGROUND OF THE INVENTION

1. Field of Invention

The invention generally relates to an estimation of a maximum friction coefficient between a tire and a road. More particularly, the invention relates to an apparatus and method for estimating the maximum friction coefficient between a tire of each wheel and the road, whether each particular wheel is a driving wheel or a driven wheel.

2. Description of Related Art

An apparatus for estimating the maximum friction coefficient between a tire and a road in vehicles such as automobiles is disclosed in, e.g., Japanese Laid-Open Publication No. HEI 3-295445. The apparatus for estimating the maximum friction coefficient as described in the aforementioned publication calculates a driving torque and a vertical load of a wheel when the wheel is placed into a predetermined acceleration slip state, and calculates the maximum friction coefficient between the road and the tire based on the calculated driving torque and vertical load. This type of maximum friction coefficient estimating apparatus is known as related art.

Such a maximum friction coefficient estimating apparatus estimates the maximum friction coefficient based on the driving torque and the vertical load of the tire at the time the driving wheel is placed into a predetermined acceleration slip state. Therefore, this apparatus is capable of accurately estimating the maximum friction coefficient between the tire and the road as compared to, for example, an apparatus for estimating a friction coefficient based on the square root of the sum of squares of the longitudinal acceleration and the lateral acceleration of the vehicle.

However, such a conventional maximum friction coefficient estimating apparatus can estimate the maximum friction coefficient only at the moment the driving wheel is placed into a predetermined acceleration slip state. Moreover, in order for this estimating apparatus to estimate the maximum friction coefficient, the wheel must be placed into the predetermined acceleration slip state. Therefore, this estimating apparatus cannot estimate the maximum friction coefficient between the tire of the driven wheel and the road.

SUMMARY OF THE INVENTION

The invention is made in view of the foregoing problems in the conventional maximum friction coefficient estimating apparatus that is configured to estimate the maximum friction coefficient based on the driving torque and the support load of the tire when drive slip occurs.

As the slip ratio of the tire increases, the road friction coefficient gets closer to the maximum friction coefficient, and the ratio of variation in reaction force of the road to variation in slip ratio gradually gets closer to zero. Moreover, provided that the reaction force of the road to the tire and the vertical load of the tire are obtained, the road friction coefficient (adhesion coefficient) can be obtained by

2 dividing the reaction force of the road by the support load. In view of these points, the invention is capable of estimating the maximum road friction coefficient regardless of whether the tire is in a predetermined acceleration slip state and whether the wheel is a driving wheel.

A controller for estimating a maximum friction coefficient according to the invention includes: a first section that calculates a reaction force of a road to a tire of a wheel based on a model of the tire; a second section that calculates a vertical load of the tire of the wheel; a third section that calculates a ratio of the reaction force of the road to the vertical load as a first ratio; a fourth section that calculates as a second ratio a ratio of variation in the reaction force of the road to variation in a slip ratio of the tire, the slip ratio being calculated based on the tire model; and a fifth section that calculates a maximum road friction coefficient based on a product of a predetermined coefficient and the second ratio, and the first ratio.

Thus, the maximum road friction coefficient is calculated regardless of whether the wheel is in a predetermined acceleration slip state. Moreover, the maximum road friction coefficient is calculated either for the driving wheel or the driven wheel.

BRIEF DESCRIPTION OF THE DRAWINGS

FIG. 13 is a flowchart illustrating a routine for estimating the maximum friction coefficient according to the second embodiment.

DETAILED DESCRIPTION OF PREFERRED EMBODIMENTS

Before describing embodiments of the invention, an outline of the maximum friction coefficient calculating apparatus according to the invention will be presented. Note that, for example purposes only, the description will be provided for the situation where a vehicle turns to the left. Regarding the longitudinal force of a tire, driving force is herein regarded as positive force, and braking force is regarded as negative force. Regarding the longitudinal acceleration, acceleration is regarded as positive acceleration and deceleration is regarded as negative acceleration. Regarding the lateral force of a tire, leftward force is regarded as positive force. Regarding the lateral acceleration, leftward acceleration is regarded as positive acceleration. Regarding the lateral slip angle of the vehicle, an angle in the counterclockwise direction is regarded as a positive angle. Regarding the steering angle, an angle in the counterclockwise direction (in the left-handed turning direction) is regarded as a positive angle.

1. Basic concept

Figure 1:
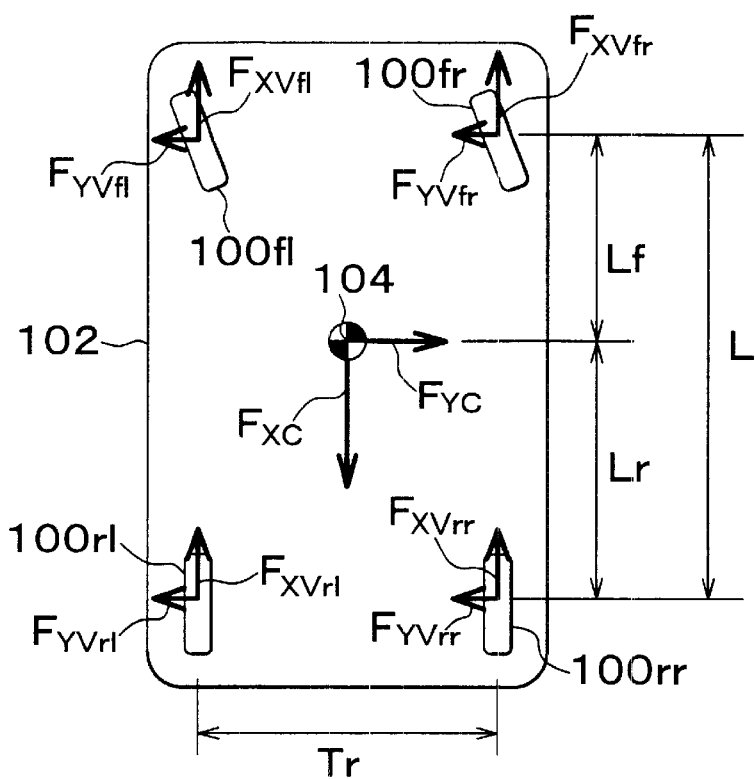
FIG. 1 is a diagram illustrating the forces applied to each wheel in the longitudinal and lateral directions of the vehicle, and the longitudinal and lateral forces applied to the vehicle at its center of gravity.

In FIG. 1, $100_{fl}$, $100_{fr}$, $100_{rl}$ and $100_{rr}$ denote left and right front wheels and left and right rear wheels of a vehicle 102, respectively. $F_{XVi}$ (i=fl, fr, rl, rr) denotes the force in the longitudinal direction of the vehicle that is applied from the road to the left and right front wheels and left and right rear wheels, respectively. $F_{YVi}$ (i=fl, fr, rl, rr) denotes the force in the lateral direction of the vehicle that is applied from the road to the left and right front wheels and left and right rear wheels, respectively. $F_{XC}$ and $F_{YC}$ denote the longitudinal force and lateral force that are applied to the vehicle 102 at its center of gravity 104, respectively.

As shown in FIG. 1, a balance of the forces in the lateral direction of the vehicle is given by the following expression (1), and the vehicle is subjected to the lateral acceleration corresponding to the lateral force $F_{YC}$:

$$F_{YC} = F_{YVfl} + F_{YVfr} + F_{YVrl} + F_{YVrr} \tag{1}$$

Similarly, a balance of the forces in the longitudinal direction of the vehicle is given by the following expression (2), and the vehicle is subjected to the longitudinal acceleration corresponding to the longitudinal force $F_{XC}$:

$$F_{XC} = F_{XVfl} + F_{XVfr} + F_{XVrl} + F_{XVrr} \tag{2}$$

As shown in FIG. 1, the tread of the vehicle is denoted with Tr, the distance between the front axle and the center of gravity 104 of the vehicle is denoted with Lf, and the distance between the rear axle and the center of gravity 104 of the vehicle is denoted with Lr. Provided that the yaw inertia moment of the vehicle is $I_B$, and the rate of change in yaw rate of the vehicle, i.e., yaw acceleration, is γd, balance of the yaw moment around the center of gravity of the vehicle resulting from the reaction force of the road to the wheels is given by the following expression (3):

$$I_B \gamma d = (F_{XVfr} - F_{XVfl} + F_{XVrr} - F_{XVrl})\frac{Tr}{2} + (F_{YVfl} + F_{YVfr})L_f - (F_{YVrl} + F_{YVrr})L_r. \tag{3}$$

(1) When $I_B \gamma d > 0$

The vehicle is subjected to the yaw acceleration in the counterclockwise direction, so that the lateral slip angle of the rear wheels is increased. The yaw acceleration is gradually reduced in such a range that the sum of the lateral forces on the left and right rear wheels, $F_{YVrl} + F_{YVrr}$, may increase due to the increased lateral slip angle of the rear wheels. The value $I_B \gamma d$ finally becomes equal to zero, so that the moment around the center of gravity balances statically. Even if the sum of the lateral forces, $F_{YVrl} + F_{YVrr}$, reaches the limit, the moment around the center of gravity cannot balance statically as long as $I_B \gamma d > 0$. Therefore, the vehicle is rendered in a spin state. Note that the limit of the sum ($F_{YVrl} + F_{YVrr}$) is affected by the longitudinal forces on the left and right rear wheels $F_{XVrl}$, $F_{XVrr}$ and the maximum road friction coefficient of the rear wheels.

A conventional rear-wheel antilock device and anti wheel-spin device also have a function to control the braking force and driving force of the rear wheels so as to ensure the sum of the lateral forces on the rear wheels, $F_{YVrl} + F_{YVrr}$. However, since these devices are not intended to optimize the value ($F_{YVrl} + F_{YVrr}$), such that the moment around the center of gravity balances statically, their spin control function is not perfect.

Therefore, the following operation may be conducted when the vehicle is rendered in a spin state: the braking force and driving force of each wheel can be controlled so that the moment around the center of gravity resulting from the reaction force of the road to the wheels balances statically. This suppresses and thus eliminates the spin state of the vehicle.

(2) When $I_B \gamma d < 0$

The vehicle is subjected to the yaw acceleration in the clockwise direction, so that the lateral slip angle of the rear wheels is reduced. The yaw acceleration is therefore gradually reduced. The value $I_B \gamma d$ finally becomes equal to zero, whereby the moment around the center of gravity balances statically.

(3) When $I_B \gamma d = 0$

In this case, the moment around the center of gravity balances statically, and the vehicle is in a stable state. Even in such a situation, the turning capability of the vehicle is not effectively obtained if the sum of the lateral forces of the left and right front wheels, $F_{YVfl} + F_{YVfr}$, reaches the limit and the sum of the lateral forces of the left and right rear wheels, $F_{YVrl} + F_{YVrr}$, does not reach the limit. This state is called a drift-out state.

A conventional front-wheel antilock device controls the braking force of the front wheels in order to ensure the sum of the lateral forces on the front wheels, $F_{YVfl} + F_{YVfr}$. As a result, the vehicle is subjected to the yaw acceleration in the counterclockwise direction, whereby the lateral slip angle of the rear wheels is increased. The front-wheel antilock device thus increases the sum of the lateral forces of the rear wheels, $F_{YVrl} + F_{YVrr}$, so as to ensure the turning capability of the vehicle. However, since this front-wheel antilock device is not intended to optimize the value ($F_{YVrl} + F_{YVrr}$), the drift-out control function thereof is not perfect.

Therefore, the following operation may be conducted when the vehicle is rendered in a drift-out state: the braking force and driving force of the rear wheels can be controlled so that the lateral slip angle of the rear wheels is increased by the angular moment on the vehicle that is produced by the difference in longitudinal force between the left and right rear wheels. The sum of the lateral forces of the rear wheels, $F_{YVrl} + F_{YVrr}$, is thus optimized. This improves the turning capability of the vehicle, suppressing and thus eliminating the drift-out state of the vehicle.

In order to determine and control the spin state and drift-out state of the vehicle based on the moment around the center of gravity of the vehicle resulting from the reaction force of the road to the wheels as described above, it is necessary to accurately keep track of the braking force and driving force of the wheels and the moment resulting from the reaction force of the road to the wheels which may cause the spin state and the drift-out state. This requires accurate estimation of the maximum road friction coefficient of each wheel for example in the manner described below.

2. Basic process

It is herein assumed that the longitudinal acceleration of the vehicle is $G_X$, the lateral acceleration of the vehicle is $G_Y$, the yaw rate of the vehicle is $\gamma$, the yaw acceleration is $\gamma d$, the steering angle is $\delta$, the wheel speed of the left and right front wheels and the left and right rear wheels is $VW_i$ (i=fl, fr, rl, rr), the wheel acceleration of the left and right front wheels and the left and right rear wheels is $VWd_i$ (i=fl, fr, rl, rr), the wheel cylinder hydraulic pressure on the left and right front wheels and the left and right rear wheels is $P_i$ (i=fl, fr, rl, rr), the lateral slip angle of the vehicle is $\beta_B$ (which is separately calculated as described below), the braking force of the left and right front wheels and the left and right rear wheels is $B_i$ (i=fl, fr, rl, rr), and the vertical load of the left and right front wheels and the left and right rear wheels is $F_{zi}$ (i=fl, fr, rl, rr).

Provided that $K_{Pf\ and\ KPr}$ respectively represent conversion coefficients (negative value) from the wheel cylinder hydraulic pressure on the front and rear wheels into the braking force, the braking forces $B_{fl}$, $B_{fr}$ of the left and right front wheels and the braking forces $B_{rl}$, $B_{rr}$ of the left and right rear wheels are respectively given by the following equations (4) to (7):

$$B_{fl} = K_{Pf} \cdot P_{fl} \quad (4)$$

$$B_{fr} = K_{Pf} \cdot P_{fr} \quad (5)$$

$$B_{rl} = K_{Pr} \cdot P_{rl} \quad (6)$$

$$B_{rr} = K_{Pr} \cdot P_{rr} \quad (7)$$

Provided that the wheelbase of the vehicle is L ($=L_f+L_r$), the height of the center of gravity of the vehicle is h, the vehicle weight is $F_{ZV}$, the gravitational acceleration is g, the roll rigidity distribution for the front wheels is $\eta_f$, and the roll rigidity distribution for the rear wheels is $\eta_r$, the vertical loads of the left and right front wheels and the left and right rear wheels, $F_{Zfl}$, $F_{Zfr}$, $F_{Zrl}$, $F_{Zrr}$, are respectively given by the following equations (8) to (11):

$$F_{Zfl} = \left(\frac{L_r - hG_X}{2L} - \eta_f \frac{h}{d} G_Y\right) \frac{F_{ZV}}{g} \quad (8)$$

$$F_{Zfr} = \left(\frac{L_r - hG_X}{2L} + \eta_f \frac{h}{d} G_Y\right) \frac{F_{ZV}}{g} \quad (9)$$

$$F_{Zrl} = \left(\frac{L_f + hG_X}{2L} - \eta_r \frac{h}{d} G_Y\right) \frac{F_{ZV}}{g} \quad (10)$$

$$F_{Zrr} = \left(\frac{L_f + hG_X}{2L} + \eta_r \frac{h}{d} G_Y\right) \frac{F_{ZV}}{g} \quad (11)$$

3. Calculation of the longitudinal force of the tire of each wheel and the driving force of the vehicle.

Figure 2:
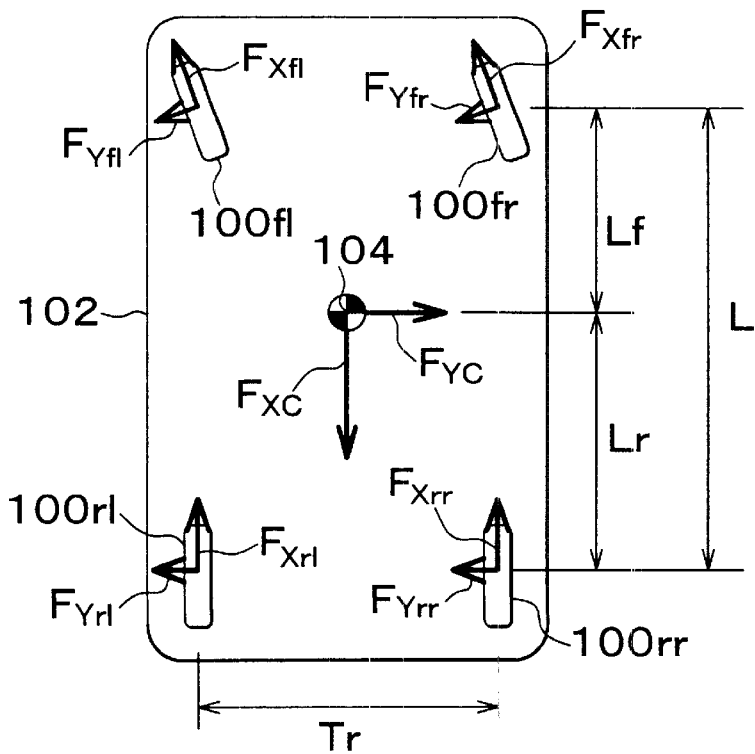
FIG. 2 is a diagram illustrating the forces applied to each wheel in the longitudinal and lateral directions of the tire, and the longitudinal and lateral forces applied to the vehicle at its center of gravity.

As shown in FIG. 2, provided that the longitudinal forces of tires of the left and right front wheels and the left and right rear wheels are $F_{Xfl}$, $F_{Xfr}$, $F_{Xrr}$, and the lateral forces of the tires of the left and right front wheels are $F_{Yfl}$, $F_{Yfr}$, the mass of the vehicle is m, and the steering angle is $\delta$, the following equation (12) is obtained from the balancing of the forces in the longitudinal direction of the vehicle:

$$mG_X = (F_{Xfl}+F_{Xfr})\cos\delta - (F_{Yfl}+F_{Yfr})\sin\delta + (F_{Xrl}+F_{Xrr}) \quad (12)$$

(1) A Rear-wheel-drive Vehicle

Provided that the effective radius of the tire is r, the driving force of the vehicle is D, and the moment of inertia of the left and right front wheels and the left and right rear wheels is $I_{Wi}$ (i=fl, fr, rl, rr), the longitudinal forces of the tires of the left and right front wheels and the left and right rear wheels, $F_{Xfl}$, $F_{Xfr}$, $F_{Xrl}$, $F_{Xrr}$, are respectively given by the following equations (13) to (16). Note that the wheel acceleration $VWd_i$ in the equations (13) to (16) and the like may be a derivative value of the corresponding wheel speed $VW_i$.

$$F_{Xfl} = B_{fl} - \frac{I_{wf} \cdot VWd_{fl}}{r^2} \quad (13)$$

$$F_{Xfr} = B_{fr} - \frac{I_{wf} \cdot VWd_{fr}}{r^2} \quad (14)$$

$$F_{Xrl} = B_{rl} + \frac{1}{2}D - \frac{I_{wr} \cdot VWd_{rl}}{r^2} \quad (15)$$

$$F_{Xrr} = B_{rr} + \frac{1}{2}D - \frac{I_{wr} \cdot VWd_{rr}}{r^2} \quad (16)$$

From the above equations (12) to (16), the longitudinal forces of the tires of the left and right front wheels and the left and right rear wheels, $F_{Xfl}$, $F_{Xfr}$, $F_{Xrl}$, $F_{Xrr}$, are respectively given by the following equations (17) to (20):

$$F_{Xfl} = B_{fl} - \frac{I_{wf} \cdot VWd_{fl}}{r^2} \quad (17)$$

$$F_{Xfr} = B_{fr} - \frac{I_{wf} \cdot VWd_{fr}}{r^2} \quad (18)$$

$$F_{Xrl} = \frac{1}{2}\left[mG_X - \left\{B_{fl} + B_{fr} - \frac{I_{wf}(VWd_{fl} + VWd_{fr})}{r^2}\right\}\cos\delta + \right. \quad (19)$$
$$\left. (F_{Yfl} + F_{Yfr})\sin\delta + (B_{rl} - B_{rr}) - \frac{I_{wr}(VWd_{rl} - VWd_{rr})}{r^2}\right]$$

$$F_{Xrr} = \frac{1}{2}\left[mG_X - \left\{B_{fl} + B_{fr} - \frac{I_{wf}(VWd_{fl} + VWd_{fr})}{r^2}\right\}\cos\delta + \right. \quad (20)$$
$$\left. (F_{Yfl} + F_{Yfr})\sin\delta + (B_{rr} - B_{rl}) - \frac{I_{wr}(VWd_{rr} - VWd_{rl})}{r^2}\right]$$

By substituting the above equations (13) to (16) for the equation (12), the driving force D of the vehicle is obtained by equation (21) as follows:

$$D = mG_X - \left\{B_{fl} + B_{fr} - \frac{I_{wf}(VWd_{fl} + VWd_{fr})}{r^2}\right\}\cos\delta + \quad (21)$$
$$(F_{Yfl} + F_{Yfr})\sin\delta - \left\{B_{rl} + B_{rr} - \frac{I_{wr}(VWd_{rl} + VWd_{rr})}{r^2}\right\}$$

(2) A Front-wheel-drive Vehicle

In the case of the front-wheel-drive vehicle, the longitudinal forces of the tires of the left and right front wheels and the left and right rear wheels $F_{Xfl}$, $F_{Xfr}$, $F_{Xrl}$, $F_{Xrr}$, are respectively given by the following equations (22) to (25):

$$F_{Xfl} = B_{fl} + \frac{1}{2}D - \frac{I_{wf} \cdot VWd_{fl}}{r^2} \quad (22)$$

$$F_{Xfr} = B_{fr} + \frac{1}{2}D - \frac{I_{wf} \cdot VWd_{fr}}{r^2} \quad (23)$$

$$F_{Xrl} = B_{rl} - \frac{I_{wr} \cdot VWd_{rl}}{r^2} \quad (24)$$

$$F_{Xrr} = B_{rr} - \frac{I_{wr} \cdot VWd_{rr}}{r^2} \quad (25)$$

From the above equations (12) and (22) to (25), the longitudinal forces of the tires of the left and right front wheels and the left and right rear wheels, $F_{Xfl}$, $F_{Xfr}$, $F_{Xrl}$, $F_{Xrr}$, are respectively given by the following equations (26) to (29):

$$F_{Xfl} = \frac{mG_X + (F_{Yfl} + F_{Yfr})\sin\delta - (B_{rl} + B_{rr}) + \frac{I_{Wr}(VWd_{rl} + VWd_{rr})}{r^2}}{2\cos\delta} + \qquad (26)$$

$$\frac{1}{2}(B_{fl} - B_{fr}) - \frac{I_{Wr}(VWd_{fl} - VWd_{fr})}{2r^2}$$

$$F_{Xfr} = \frac{mG_X + (F_{Yfl} + F_{Yfr})\sin\delta - (B_{rl} + B_{rr}) + \frac{I_{Wr}(VWd_{rl} + VWd_{rr})}{r^2}}{2\cos\delta} - \qquad (27)$$

$$\frac{1}{2}(B_{fl} - B_{fr}) + \frac{I_{Wr}(VWd_{fl} - VWd_{fr})}{2r^2}$$

$$F_{Xrl} = B_{rl} - \frac{I_{Wr} \cdot VWd_{rl}}{r^2} \qquad (28)$$

$$F_{Xrr} = B_{rr} - \frac{I_{Wr} \cdot VWd_{rr}}{r^2}. \qquad (29)$$

By substituting the above equations (22) to (25) for the equation (12), the driving force D of the vehicle can be obtained by equation (30) as follows:

$$D = \frac{mG_X + (F_{Yfl} + F_{Yfr})\sin\delta - (B_{rl} + B_{rr}) + \frac{I_{Wr}(VWd_{rl} + VWd_{rr})}{r^2}}{\cos\delta} - \qquad (30)$$

$$(B_{fl} + B_{fr}) + \frac{I_{Wf}(VWd_{fl} + VWd_{fr})}{r^2}.$$

As can be seen from the foregoing description, by using the previous calculated values of the lateral forces of the tires of the front wheels $F_{Yfl}$ and $F_{Yfr}$ in the above equations, the longitudinal acceleration of the vehicle $G_X$, the steering angle $\delta$, the brake hydraulic pressure $P_i$ of each wheel, and the wheel acceleration $VWd_i$ are detected. Accordingly, the longitudinal force of the tire of each wheel, $F_{xi}$ is calculated according to the equations (17) to (20) or the equations (26) to (29). In this case, the engine and the driving system need not be taken into account even when driving the vehicle. Moreover, the driving force that is transmitted from the engine to the axle of the driving wheels through the driving system can be calculated according to the above equation (21) or (30). In this case, the driving force of the axle of the driving wheels can be calculated without taking into account the engine map, gear ratio of the driving system, and transmission efficiency.

4. Calculation of the Lateral Force of the Tire of Each Wheel

The following equations (31) and (32) are obtained from the balancing of the forces in the lateral direction of the vehicle and the balancing of the yaw moment around the center of gravity:

$$mG_Y = F_{YVfl} + F_{YVfr} + F_{YVrl} + F_{YVrr} \qquad (31)$$

$$I_B\gamma d = \frac{Tr}{2}(F_{XVfr} - F_{XVfl}) + L_f(F_{YVfl} + F_{YVfr}) + \qquad (32)$$

$$\frac{Tr}{2}(F_{XVrr} - F_{XVrl}) - L_r(F_{YVrl} + F_{YVrr}).$$

(1) The Lateral Forces of the Tires of the Front Wheels

The above equation (32) is rewritten as equation (33) as follows:

$$I_B\gamma d = \frac{Tr}{2}(F_{XVfr} - F_{XVfl}) + L_f(F_{YVfl} + F_{YVfr}) + \qquad (33)$$

$$\frac{Tr}{2}(F_{XVrr} - F_{XVrl}) - L_r(mG_Y - F_{YVfl} - F_{YVfr})$$

$$= \frac{Tr}{2}(F_{XVfr} - F_{XVfl} + F_{XVrr} - F_{XVrl}) +$$

$$L(F_{YVfl} + F_{YVfr}) - L_r mG_Y.$$

Substituting the following equations (34) to (37) for the equation (33) results in the following equation (38):

$$F_{XVfl} = F_{Xfl}\cos\delta - F_{Yfl}\sin\delta \qquad (34)$$

$$F_{XVfr} = F_{Xfr}\cos\delta - F_{Yfr}\sin\delta \qquad (35)$$

$$F_{XVfl} = F_{Xfl}\cos\delta + F_{Yfl}\cos\delta \qquad (36)$$

$$F_{XVfr} = F_{Xfr}\sin\delta + F_{Yfr}\sin\delta \qquad (37)$$

$$\left(\cos\delta + \frac{Tr}{2L}\sin\delta\right)F_{Yfl} + \left(\cos\delta - \frac{Tr}{2L}\sin\delta\right)F_{Yfr} = \qquad (38)$$

$$\frac{I_B\gamma d + L_r mG_Y - \frac{Tr}{2}(F_{Xrr} - F_{Xrl})}{L} -$$

$$\left(\sin\delta - \frac{Tr}{2L}\cos\delta\right)F_{Xfl} - \left(\sin\delta + \frac{Tr}{2L}\cos\delta\right)F_{Xfr}.$$

Provided that the respective coefficients of the lateral forces on tires $F_{Yfl}$, $F_{Yfr}$ in the equation (38) are $A_k$ and $B_k$ and the right side of the equation (38) is $C_k$, the equation (38) is rewritten as the following equation (39). Note that, in the practical range of the steering angle, $A_k > 0$ and $B_k > 0$ $$A_k F_{Yfl} + B_k F_{Yfr} = C_k \qquad (39)$$

In general, the ratio of the reaction force of the road between the left and right front wheels corresponds to the ratio of the vertical loads between the left and right front wheels (or the ratio between the products of the maximum road friction coefficient and the respective vertical loads). Therefore, the following equation (40) is obtained:

$$(F_{Xfl}^2 + F_{Yfl}^2)\left(\frac{F_{Zfr}}{F_{Zfl}}\right)^2 = F_{Xfr}^2 + F_{Yfr}^2. \qquad (40)$$

Substituting $F_{Yfr}$ in the equation (39) for the equation (40) results in the following equation (41), whereby the following equation (42) is obtained:

$$(F_{Xfl}^2 + F_{Yfl}^2)\left(\frac{F_{Zfr}}{F_{Zfl}}\right)^2 = F_{Xfr}^2 + \left(\frac{C_k - A_k \cdot F_{Yfl}}{B_k}\right)^2 \qquad (41)$$

$$\left\{\left(\frac{A_k}{B_k}\right)^2 - \left(\frac{F_{Zfr}}{F_{Zfl}}\right)^2\right\}F_{Yfl}^2 - \frac{2A_k C_k}{B_k^2} F_{Yfl} + \left(\frac{C_k}{B_k}\right)^2 + F_{Xfr}^2 - \left(\frac{F_{Zfr}}{F_{Zfl}}\right)^2 F_{Xfl}^2 = 0$$

$$F_{Xfl}^2 = \frac{\frac{A_k C_k}{B_k^2} \pm \sqrt{\left(\frac{F_{Zfr}}{F_{Zfl}}\right)^2 \left\{\left(\frac{C_k}{B_k}\right)^2 + F_{Xfr}^2 + \left(\frac{A_k}{B_k}\right)^2 F_{Xfl}^2\right\} - \left(\frac{F_{Zfr}}{F_{Zfl}}\right)^4 F_{Xfr}^2 - \left(\frac{A_k}{B_k}\right)^2 F_{Xfr}^2}}{\left(\frac{A_k}{B_k}\right)^2 - \left(\frac{F_{Zfr}}{F_{Zfl}}\right)^2}. \qquad (42)$$

Similarly substituting $F_{Yfl}$ in the equation (39) for the equation (40) results in the following equation (43):

$$F_{Yfr} = \frac{\frac{B_k C_k}{A_k^2} \pm \sqrt{\left(\frac{F_{Zfl}}{F_{Zfr}}\right)^2 \left\{\left(\frac{C_k}{B_k}\right)^2 + F_{Xfl}^2 + \left(\frac{B_k}{A_k}\right)^2 F_{Xfr}^2\right\} - \left(\frac{F_{Zfl}}{F_{Zfr}}\right)^4 F_{Xfr}^2 - \left(\frac{B_k}{A_k}\right)^2 F_{Xfl}^2}}{\left(\frac{B_k}{A_k}\right)^2 - \left(\frac{F_{Zfr}}{F_{Zfl}}\right)^2}. \qquad (43)$$

While the vehicle is turning to the left, $C_k>0$, $F_{Yfl}>0$ and $F_{Yfr}>0$. When the following expression (44) is satisfied, the denominator in the above equation (43) is negative. In order to satisfy $F_{Yrr}>0$, the sign "±" in the equation (43) must be negative "−". Accordingly, the lateral force of the tire of the right front wheel, $F_{Yfr}$, is obtained by the following equation (45), and the lateral force of the tire of the left front wheel, $F_{Yfl}$, is obtained by the following equation (46):

When the following expression (47) is satisfied, the denominator in the above equation (42) is negative. Therefore, in order to satisfy $F_{Yrl}>0$, the sign "±" in the equation (42) must be negative "−". Accordingly, the lateral force of the tire of the left front wheel, $F_{Yfl}$, is obtained by the following equation (48), and the lateral force of the tire of the right front wheel, $F_{Yfr}$, is obtained by the following equation (49):

$$\left(\frac{A_k}{B_k}\right)^2 - \left(\frac{F_{Zfr}}{F_{Zfl}}\right)^2 > 0 \qquad (44)$$

$$F_{Yfr} = \frac{\frac{B_k C_k}{A_k^2} - \sqrt{\left(\frac{F_{Zfl}}{F_{Zfr}}\right)^2 \left\{\left(\frac{C_k}{A_k}\right)^2 + F_{Xfl}^2 + \left(\frac{B_k}{A_k}\right)^2 F_{Xfr}^2\right\} - \left(\frac{F_{Zfl}}{F_{Zfr}}\right)^4 F_{Xfr}^2 - \left(\frac{B_k}{A_k}\right)^2 F_{Xfl}^2}}{\left(\frac{B_k}{A_k}\right)^2 - \left(\frac{F_{Zfl}}{F_{Zfr}}\right)^2} \qquad (45)$$

$$F_{Yfl} = \frac{C_k - B_k \cdot F_{Yfr}}{A_k}. \qquad (46)$$

$$\left(\frac{A_k}{B_k}\right)^2 - \left(\frac{F_{Zfr}}{F_{Zfl}}\right)^2 < 0 \tag{47}$$

$$F_{Yfl} = \frac{\frac{A_k C_k}{B_k^2} - \sqrt{\left(\frac{F_{Zfr}}{F_{Zfl}}\right)^2 \left\{\left(\frac{C_k}{B_k}\right)^2 + F_{Xfr}^2 + \left(\frac{A_k}{B_k}\right)^2 F_{Xfl}^2\right\} - \left(\frac{F_{Zfr}}{F_{Zfl}}\right)^4 F_{Xfr}^2 - \left(\frac{A_k}{B_k}\right)^2 F_{Xfr}^2}}{\left(\frac{A_k}{B_k}\right)^2 - \left(\frac{F_{Zfr}}{F_{Zfl}}\right)^2} \tag{48}$$

$$F_{Yfr} = \frac{C_k - A_k \cdot F_{Yfl}}{B_k}. \tag{49}$$

While the vehicle is turning to the right, $C_k<0$, $F_{Yfl} \geq 0$ and $F_{Yfr}<0$. When the above expression (44) is satisfied, the denominator in the above equation (43) is negative. Therefore, in order to satisfy $F_{Yfr}<0$, the sign "±" in the equation (43) must be positive "+". Accordingly, the lateral force of the tire of the right front wheel, $F_{Yfr}$, is obtained by the following equation (50), and the lateral force of the tire of the left front wheel, $F_{Yfl}$, is obtained by the following equation (51):

$$F_{Yfr} = \frac{\frac{B_k C_k}{A_k^2} - \sqrt{\left(\frac{F_{Zfl}}{F_{Zfr}}\right)^2 \left\{\left(\frac{C_k}{A_k}\right)^2 + F_{Xfl}^2 + \left(\frac{B_k}{A_k}\right)^2 F_{Xfr}^2\right\} - \left(\frac{F_{Zfl}}{F_{Zfr}}\right)^4 F_{Xfr}^2 - \left(\frac{B_k}{A_k}\right)^2 F_{Xfl}^2}}{\left(\frac{B_k}{A_k}\right)^2 - \left(\frac{F_{Zfl}}{F_{Zfr}}\right)^2} \tag{50}$$

$$F_{Yfl} = \frac{C_k - B_k \cdot F_{Yfr}}{A_k}. \tag{51}$$

When the above expression (47) is satisfied, the denominator in the above equation (42) is negative. Therefore, in order to satisfy $F_{Yfl}<0$, the sign "±" in the equation (42) must be positive "+". Accordingly, the lateral force of the tire of the left front wheel, $F_{Yfl}$, is obtained by the following equation (52), and the lateral force of the tire of the right front wheel, $F_{Yfr}$, is obtained by the following equation (53):

$$F_{Yfl} = \frac{\frac{A_k C_k}{B_k^2} + \sqrt{\left(\frac{F_{Zfr}}{F_{Zfl}}\right)^2 \left\{\left(\frac{C_k}{B_k}\right)^2 + F_{Xfr}^2 + \left(\frac{A_k}{B_k}\right)^2 F_{Xfl}^2\right\} - \left(\frac{F_{Zfr}}{F_{Zfl}}\right)^4 F_{Xfr}^2 - \left(\frac{A_k}{B_k}\right)^2 F_{Xfr}^2}}{\left(\frac{A_k}{B_k}\right)^2 - \left(\frac{F_{Zfr}}{F_{Zfl}}\right)^2} \tag{52}$$

$$F_{Yfl} = \frac{C_k - A_k \cdot F_{Yfl}}{B_k}. \tag{53}$$

(2) The Lateral Forces of the Tires of the Rear Wheels

The above equation (32) is rewritten as equation (54) as follows:

$$I_B \gamma d = \frac{Tr}{2}(F_{XVfr} - F_{XVfl}) + L_f(F_{YVfl} + F_{YVfr}) + \tag{54}$$
$$\frac{Tr}{2}(F_{XVrr} - F_{XVrl}) + L_f(F_{YVrl} + F_{YVrr})$$
$$= \frac{Tr}{2}(F_{XVfr} - F_{XVfl}) + L_f(mG_Y - F_{YVrl} - F_{YVrr}) +$$
$$\frac{Tr}{2}(F_{XVrr} - F_{XVrl}) - L_r(F_{YVrl} + F_{YVrr}).$$

Substituting the following equations (55) to (60) for the equation (54) results in the following equation (61). Note that the values calculated in "(1) The lateral forces of the tires of the front wheels" are used $F_{Yfl}$ and $F_{Yfr}$ in the equations (55) and (56).

$$F_{XVfl}=F_{Xfl} \cos \delta - F_{Yfl} \sin \delta \tag{55}$$
$$F_{XVfr}=F_{Xfr} \cos \delta - F_{Yfr} \sin \delta \tag{56}$$
$$F_{XVrl}=F_{Xrl} \tag{57}$$
$$F_{XVrr}=F_{Xrr} \tag{58}$$
$$F_{YVrl}=F_{Yrl} \tag{59}$$
$$F_{YVrl}=F_{Yrr} \tag{60}$$

$$F_{Yrl} + F_{Yrr} = \frac{-I_B \gamma d + L_f m G_Y + \frac{Tr}{2}\{(F_{Xfr} - F_{Xfl})\cos\delta - (F_{Yfr} - F_{Yfl})\sin\delta\}}{L}. \tag{61}$$

Provided that the right side of the equation (61) is $D_k$, the equation (61) is rewritten as equation (62) as follows:

$$F_{Yrl}+F_{Yrr}=D_k \tag{62}$$

In general, the ratio of the reaction force of the road between the left and right rear wheels also corresponds to the ratio of the vertical loads between the left and right rear wheels (or the ratio of the products of the maximum road friction coefficient and the respective vertical loads). Therefore, the following equations (63) and (64) are obtained:

$$(F_{Xrl}^2 + F_{Yrl}^2)\left(\frac{F_{Zrr}}{F_{Zrl}}\right)^2 = F_{Xrr}^2 + F_{Yrr}^2 = F_{Xrr}^2 + (D_k - F_{Yrl})^2 \tag{63}$$

$$\left\{1 - \left(\frac{F_{Zrr}}{F_{Zrl}}\right)^2\right\}F_{Yrl}^2 - 2D_k F_{Yrl} + D_k^2 + F_{Xrr}^2 - \left(\frac{F_{Zrr}}{F_{Zrl}}\right)^2 F_{Xrl}^2 = 0. \tag{64}$$

Substituting $F_{Yrr}$ in the above equation (62) for the equation (64) results in the following equation (65):

$$F_{Yfl} = \frac{D_k \pm \sqrt{\left(\frac{F_{Zrr}}{F_{Zrl}}\right)^2 (D_k^2 + F_{Xrl}^2 + F_{Xrr}^2) - F_{Xrr}^2 - \left(\frac{F_{Zrr}}{F_{Zrl}}\right)^4 F_{Xrl}^2}}{1 - \left(\frac{F_{Zrr}}{F_{Zrl}}\right)^2}. \quad (65)$$

Similarly, substituting $F_{Yrl}$ in the above equation (62) for the equation (64) results in the following equation (66):

$$F_{Yrr} = \frac{D_k \pm \sqrt{\left(\frac{F_{Zrl}}{F_{Zrr}}\right)^2 (D_k^2 + F_{Xrl}^2 + F_{Xrr}^2) - F_{Xrl}^2 - \left(\frac{F_{Zrl}}{F_{Zrr}}\right)^4 F_{Xrr}^2}}{1 - \left(\frac{F_{Zrl}}{F_{Zrr}}\right)^2}. \quad (66)$$

While the vehicle is turning to the left, $D_k > 0$, $F_{Yrl} > 0$ and $F_{Yrr} > 0$. When the following expression (67) is satisfied, the denominator in the above equation (66) is negative. Therefore, in order to satisfy $F_{Yrr} > 0$, the sign "±" in the equation (66) must be negative "−". Accordingly, the lateral force of the tire of the right rear wheel, $F_{Yrr}$, is obtained by the following equation (68), and the lateral force of the tire of the left rear wheel, $F_{Yrl}$, is obtained by the following equation (69):

$$1 - \left(\frac{F_{Zrr}}{F_{Zrl}}\right)^2 > 0 \quad (67)$$

$$F_{Yrr} = \frac{D_k - \sqrt{\left(\frac{F_{Zrl}}{F_{Zrr}}\right)^2 (D_k^2 + F_{Xrl}^2 + F_{Xrr}^2) - F_{Xrl}^2 - \left(\frac{F_{Zrl}}{F_{Zrr}}\right)^4 F_{Xrr}^2}}{1 - \left(\frac{F_{Zrl}}{F_{Zrr}}\right)^2} \quad (68)$$

$$F_{Yrl} = D_k - F_{Yrr} \quad (69).$$

When the following expression (70) is satisfied, the denominator in the above equation (65) is negative. Therefore, in order to satisfy $F_{Yrl} > 0$, the sign "±" in the equation (65) must be negative "−". Accordingly, the lateral force of the tire of the left rear wheel, $F_{Yrl}$, is obtained by the following equation (71), and the lateral force of the tire of the right rear wheel, $F_{Yrr}$ is obtained by the following equation (72):

$$1 - \left(\frac{F_{Zrr}}{F_{Zrl}}\right)^2 < 0 \quad (70)$$

$$F_{Yrl} = \frac{D_k - \sqrt{\left(\frac{F_{Zrr}}{F_{Zrl}}\right)^2 (D_k^2 + F_{Xrl}^2 + F_{Xrr}^2) - F_{Xrr}^2 - \left(\frac{F_{Zrr}}{F_{Zrl}}\right)^4 F_{Xrl}^2}}{1 - \left(\frac{F_{Zrr}}{F_{Zrl}}\right)^2} \quad (71)$$

$$F_{Yrr} = D_k - F_{Yrl} \quad (72).$$

While the vehicle is turning to the right, $D_k < 0$, $F_{Yrl} < 0$ and $F_{Yrr} < 0$. When the above expression (67) is satisfied, the denominator in the above equation (66) is negative. Therefore, in order to satisfy $F_{Yrr} < 0$, the sign "±" in the equation (66) must be positive "+". Accordingly, the lateral force of the tire of the right rear wheel, $F_{Yrr}$, is obtained by the following equation (73), and the lateral force of the tire of the left rear wheel, $F_{Yrl}$, is obtained by the following equation (74):

$$F_{Yrr} = \frac{D_k + \sqrt{\left(\frac{F_{Zrl}}{F_{Zrr}}\right)^2 (D_k^2 + F_{Xrl}^2 + F_{Xrr}^2) - F_{Xrl}^2 - \left(\frac{F_{Zrl}}{F_{Zrr}}\right)^4 F_{Xrr}^2}}{1 - \left(\frac{F_{Zrl}}{F_{Zrr}}\right)^2} \quad (73)$$

$$F_{Yrl} = D_k - F_{Yrr} \quad (74).$$

When the above expression (70) is satisfied, the denominator in the above equation (65) is negative. Therefore, in order to satisfy $F_{Yrl} < 0$, the sign "±" in the equation (65) must be positive "+". Accordingly, the lateral force of the tire of the left rear wheel, $F_{Yrl}$, is obtained by the following equation (75), and the lateral force of the tire of the right rear wheel, $F_{Yrr}$, is obtained by the following equation (76):

$$F_{Yrl} = \frac{D_k + \sqrt{\left(\frac{F_{Zrr}}{F_{Zrl}}\right)^2 (D_k^2 + F_{Xrl}^2 + F_{Xrr}^2) - F_{Xrr}^2 - \left(\frac{F_{Zrr}}{F_{Zrl}}\right)^4 F_{Xrl}^2}}{1 - \left(\frac{F_{Zrr}}{F_{Zrl}}\right)^2} \quad (75)$$

$$F_{Yrr} = D_k - F_{Yrl} \quad (76).$$

5. Calculation of the Reaction Force of the Road to the Tires

The reaction force of the road to the tire of each wheel, $F_{XYi}$, (i=fl, fr, rl, rr) is obtained as the resultant force of the longitudinal force $F_{Xi}$ and the lateral force $F_{Yi}$ (i.e., the resultant reaction force of the road) by the following equations (77) to (80):

$$F_{XYfl} = \sqrt{F_{Xfl}^2 + F_{Yfl}^2} \quad (77)$$

$$F_{XYfr} = \sqrt{F_{Xfr}^2 + F_{Yfr}^2} \quad (78)$$

$$F_{XYrl} = \sqrt{F_{Xrl}^2 + F_{Yrl}^2} \quad (79)$$

$$F_{XYrr} = \sqrt{F_{Xrr}^2 + F_{Yrr}^2}. \quad (80)$$

6. Tire Model (Part 1)

According to the "brush tire model" (the equations upon driving in the section 2 above) described in "Vehicle Dynamics and Control" (Masato ABE, Sankaido), provided that VB is a vehicle speed, $\beta$ is a lateral slip angle of the tire, $K_\beta$ is lateral rigidity of the tire, $K_S$ is longitudinal rigidity of the tire, $\mu_{max}$ is the maximum road friction coefficient and $F_Z$ is vertical load of the tire, a slip ratio S and a composite slip ratio $\lambda$ are respectively given by the following equations (81) and (82). Moreover, $\xi$ is defined by the following equation (83):

$$S = \frac{VB - VW}{VW} \quad (81)$$

$$\lambda = \sqrt{S^2(1+S)^2 \left(\frac{K_\beta}{K_S}\right)^2 \tan^2\beta} \quad (82)$$

$$\xi = 1 - \frac{K_S}{3\mu_{max}F_Z}\lambda. \quad (83)$$

Figure 3A:
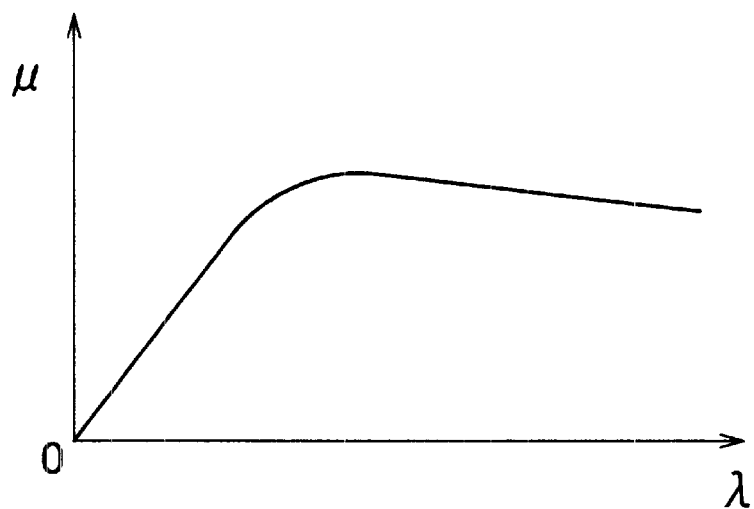
FIGS. 3A and 3B are graphs showing the relationship between a friction coefficient $\mu$ between a road and a tire, and a composite slip ratio $\lambda$ in the case of a common road A and a tire model B of the invention.
Figure 3B:
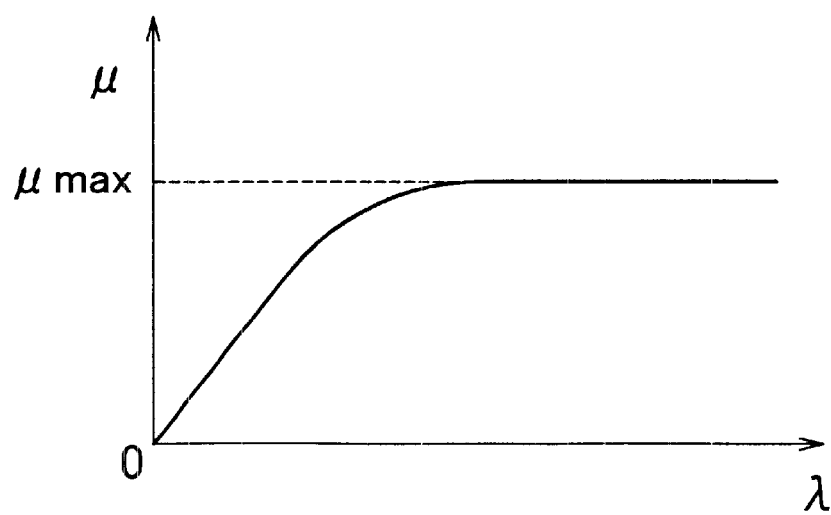

Note that the composite slip ratio $\lambda$ is a slip ratio in the direction along the reaction force $F_{XYi}$ of the road to the tire. In general, the relation between the friction coefficient $\mu$ between the tire and the road and the composite slip ratio $\lambda$ is as shown in FIG. 3A. According to the tire model, however, the relation between the friction coefficient $\mu$ and the composite slip ratio $\lambda$ is as shown in FIG. 3B, and the maximum road friction coefficient $\mu_{max}$ is defined as shown in FIG. 3B.

When $\xi > 0$, the longitudinal force $F_X$ and the lateral force $F_Y$ of the tire are respectively given by the following equations (84) and (85), provided that the reaction force of the road to the tire is applied at an angle $\theta$ with respect to the longitudinal direction of the tire:

$$F_X = -K_S S \xi^2 - 6\mu_{max}F_Z \cos\theta(\tfrac{1}{6} - \tfrac{1}{2}\xi^2 + \tfrac{1}{3}\xi^3) \quad (84)$$

$$F_Y = -K_\beta(1+S)\tan\beta \cdot \xi^2 - 6\mu_{max}F_Z \sin\theta(\tfrac{1}{6} - \tfrac{1}{2}\xi^2 + \tfrac{1}{3}\xi^3) \quad (85).$$

When $\xi \leq 0$, the longitudinal force $F_X$ and the lateral force $F_Y$ of the tire are respectively given by the following equations (86) and (87), where $\cos\theta$ and $\sin\theta$ are respectively given by the following equations (88) and (89):

$$F_X = -\mu_{max}F_Z \cos\theta \quad (86)$$

$$F_Y = -\mu_{max}F_Z \sin\theta \quad (87)$$

$$\cos\theta = S/\lambda \quad (88)$$

$$\sin\theta = \frac{K_\beta \tan\beta \cdot (1+S)}{K_S \lambda}. \quad (89)$$

The foregoing description is given by the aforementioned publication. The above equations (84) and (85) can be respectively rewritten as the following equations (90) and (91):

$$F_X = -K_S S \xi^2 - 6\mu_{max}F_Z \cos\theta \cdot (\tfrac{1}{6} - \tfrac{1}{2}\xi^2 + \tfrac{1}{3}\xi^3)$$

$$F_X = -K_S S \xi^2 - 6\mu_{max}F_Z \cos\theta \cdot \left(\frac{1}{6} - \frac{1}{2}\xi^2 + \frac{1}{3}\xi^3\right) \quad (90)$$

$$= -K_S S \left\{\xi^2 + \frac{6\mu_{max}F_Z}{K_S\lambda}\left(\frac{1}{6} - \frac{1}{2}\xi^2 + \frac{1}{3}\xi^3\right)\right\}$$

$$F_Y = -K_\beta(1+S)\tan\beta \cdot \xi^2 - 6\mu_{max}F_Z \sin\theta \cdot \left(\frac{1}{6} - \frac{1}{2}\xi^2 + \frac{1}{3}\xi^3\right) \quad (91)$$

$$= -K_\beta(1+S)\tan\beta\left\{\xi^2 + \frac{6\mu_{max}F_Z}{K_S\lambda}\left(\frac{1}{6} - \frac{1}{2}\xi^2 + \frac{1}{3}\xi^3\right)\right\}.$$

Accordingly, the reaction force of the road to the tire, $F_{XY}$, can be given by the following equation (93) based on the following equation of squares (92):

$$F_{XY}^2 = F_X^2 + F_Y^2 \quad (92)$$

$$= \{K_S^2 S^2 + K_\beta^2(1+S)^2\tan^2\beta\}\left\{\xi^2 + \frac{6\mu_{max}F_Z}{K_S\lambda}\left(\frac{1}{6} - \frac{1}{2}\xi^2 + \frac{1}{3}\xi^3\right)\right\}^2$$

$$= K_S^2 \lambda^2 \left\{\xi^2 + \frac{6\mu_{max}F_Z}{K_S\lambda}\left(\frac{1}{6} - \frac{1}{2}\xi^2 + \frac{1}{3}\xi^3\right)\right\}^2.$$

$$F_{XY} = K_S\lambda\left\{\xi^2 + \frac{6\mu_{max}F_Z}{K_S\lambda}\left(\frac{1}{6} - \frac{1}{2}\xi^2 + \frac{1}{3}\xi^3\right)\right\}. \quad (93)$$

The equation (93) and the equations (90), (91) lead to the following equations (94) and (95). The longitudinal force $F_X$ and the lateral force $F_Y$ of the tire can thus be obtained from these equations:

$$F_X = -\frac{K_S S}{K_S \lambda} F_{XY} \quad (94)$$

$$= -\frac{S}{\lambda} F_{XY}$$

$$F_Y = -\frac{K_\beta(1+S)\tan\beta}{K_S \lambda} F_{XY} \quad (95)$$

$$= -\frac{K_\beta}{K_S}\tan\beta \cdot \frac{1+S}{\lambda} F_{XY}.$$

From the above equation (83), the composite slip ratio $\lambda$ is given by the following equation (96). By substituting the composite slip ratio $\lambda$ for the above equation (93), the reaction force of the road to the tire, $F_{XY}$, is obtained as the following equation (97):

$$\lambda = (1-\xi)3\mu_{max}\frac{F_Z}{K_S} \quad (96)$$

$$F_{XY} = (1-\xi)3\mu_{max}F_Z\left\{\xi^2 + \frac{6\mu_{max}F_Z}{K_S(1-\xi)3\mu_{max}\frac{F_Z}{K_S}}\left(\frac{1}{6} - \frac{1}{2}\xi^2 + \frac{1}{3}\xi^3\right)\right\} \quad (97)$$

$$= (1-\xi)3\mu_{max}F_Z\left\{\xi^2 + \frac{2}{(1-\xi)}\left(\frac{1}{6} - \frac{1}{2}\xi^2 + \frac{1}{3}\xi^3\right)\right\}$$

$$= \mu_{max}F_Z(1-\xi^3).$$

The following equation (98) is obtained from the above equations (94) and (95), and the following equation (99) is obtained from the above equation (97):

$$F_Y = \frac{1+S}{S}\frac{K_\beta}{K_S}\tan\beta \cdot F_X \quad (98)$$

$$\frac{\partial F_{XY}}{\partial \lambda} = \frac{\partial F_{XY}}{\partial \xi}\frac{\partial \xi}{\partial \lambda} \quad (99)$$

$$= -3\mu_{max}F_Z\xi^2 \cdot -\frac{K_S}{3\mu_{max}F_Z}$$

$$= K_S\xi^2.$$

Figure 4:
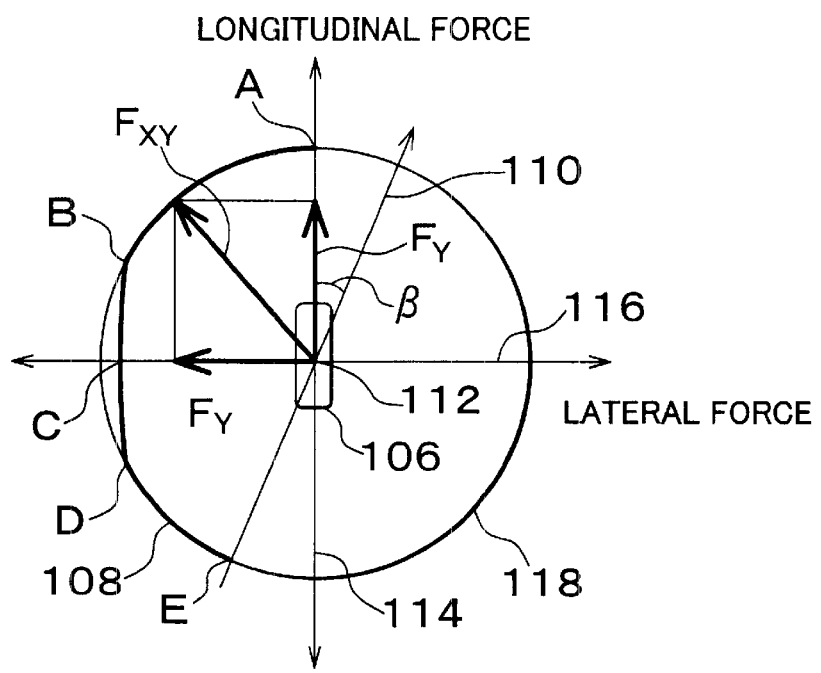
FIG. 4 is a diagram illustrating a critical friction circle of the tire, moving direction of the tire, and reaction force of the road to the tire.

FIG. 4 shows a critical friction circle 108 of a tire 106. Arrow 110 indicates the moving direction of the tire. The points A and C respectively indicate intersections of the critical friction circle 108 and lines 114, 116. The line 114 extends in the longitudinal direction of the tire, the line 116 extends in the lateral direction of the tire, and both lines 114, 116 pass through a ground contact point 112 of the tire. The point E indicates an intersection of the moving direction 110 of the tire and the critical friction circle 108. The points B and D respectively indicate the points on a perfect circle 118, which are located closest to point C among the points on the critical friction circle 108.

When ξ>0, the above equations (94), (95), (97), (98) and (99) respectively represent the values in the case where the tip of the vector of the reaction force of the road to the tire, $F_{XY}$, is located between the points B and D on the critical friction circle 108.

When ξ≦0, the reaction force of the road to the tire, $F_{XY}$, is given by the following equation (100) based on the above equations (84) and (85). The longitudinal force of the tire, $F_X$, is given by the following equation (101) based on the above equations (86) and (88). The lateral force of the tire, $F_Y$, is given by the following equation (102) based on the above equations (87) and (89):

$$F_{XY} = \mu_{max} F_Z \quad (100)$$

$$F_X = -S/\lambda F_{XY} \quad (101)$$

$$F_Y = -\frac{K_\beta}{K_S}\tan\beta \cdot \frac{1+S}{\lambda} F_{XY}. \quad (102)$$

The following equation (103) is obtained from the above equations (101) and (102), and the following equation (104) is also obtained:

$$F_Y = \frac{1+S}{S} \frac{K_\beta}{K_S}\tan\beta \cdot F_X \quad (103)$$

$$\frac{\partial F_{XY}}{\partial \lambda} = 0. \quad (104)$$

The above equations (100) to (104) for ξ<0 respectively represent the values in the case where the tip of the vector of the reaction force of the road to the tire, $F_{XY}$, is located between the points A and B or between the points D and E on the critical friction circle 108.

Note that it can be seen from the above equations (99) and (104) that $\partial F_{XY}/\partial \lambda$ is obtained by obtaining the maximum road friction coefficient $\mu_{max}$ (see the section 11 below), the vertical load $F_Z$ (see the section 2 above), the slip ratio S (see the section 10 below), the lateral slip angle β of the tire (see the section 8 below), the longitudinal rigidity $K_S$ and lateral rigidity $K_\beta$ of the tire (see the section 7 below).

7. Calculation of the Tire Rigidity

The longitudinal rigidity $K_S$ and lateral rigidity $K_\beta$ of the tire are functions of the reaction force of the road to the tire, $F_{XY}$, and the vertical load $F_Z$. It is herein assumed that $K_S$ and $K_\beta$ are respectively given by the following equations (105) and (106), provided that $K_{XYS}$ and $K_{XY\beta}$ are coefficients of the reaction force of the road $F_{XY}$, and $K_Z$, and $K_{Z\beta}$ are coefficients of the vertical load $F_Z$. Note that this assumption does not go against the facts.

$$K_S = K_{XYS} \cdot F_{XY} + K_{ZS} \cdot F_Z \quad (105)$$

$$K_\beta = K_{XY\beta} \cdot F_{XY} + K_{Z\beta} \cdot F_Z \quad (106)$$

8. Calculation of the Lateral Slip Angle of the Tire of Each Wheel

Figure 5:
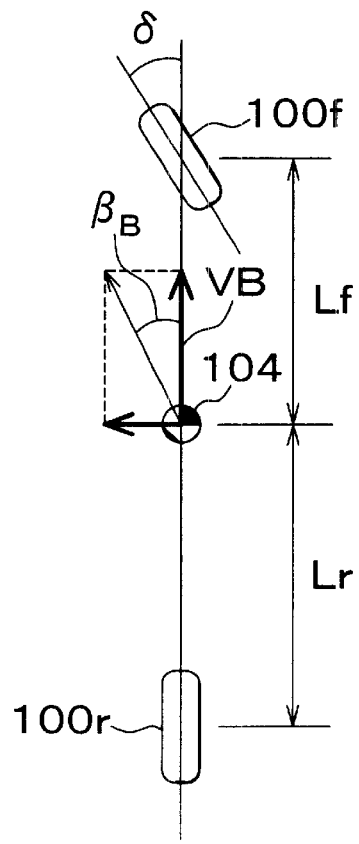
FIG. 5 is a diagram illustrating a method for calculating a lateral slip angle $\beta_i$ of each wheel based on a lateral slip angle $\beta_B$ and the like of the vehicle.

It is herein assumed that the lateral slip angle of the left wheel is equal to that of the right wheel. Based on the estimated vehicle speed VB in the section 10 below, the lateral slip angle $\beta_B$ of the vehicle and the steering angle δ, the lateral slip angles $\beta_{fl}$, $\beta_{fr}$ of the left and right front wheels (the lateral slip angle $\beta_f$ of the front wheels) as well as the lateral slip angles $\beta_{rl}$, $\beta_{rr}$ of the left and right rear wheels (the lateral slip angle $\beta_r$ of the rear wheels) can be respectively obtained by the following equations (107) and (108) (see FIG. 5):

$$\beta_{fl} = \beta_{fr} = \beta_f = \arctan\frac{VB\tan\beta_B + L_f\gamma}{VB} - \delta \quad (107)$$

$$= \arctan\left(\tan\beta_B + \frac{L_f\gamma}{VB}\right) - \delta$$

$$\beta_{rl} = \beta_{rr} = \beta_r = \arctan\frac{VB\tan\beta_B - L_r\gamma}{VB} - \delta \quad (108)$$

$$= \arctan\left(\tan\beta_B - \frac{L_r\gamma}{VB}\right).$$

Note that the lateral slip angle $\beta_B$ of the vehicle may be calculated by any method known to those skilled in the art. For example, a deviation of the lateral acceleration as a deviation $G_Y - V_\gamma$ of the lateral acceleration $G_Y$ from the product $V_\gamma$ of the vehicle speed V and the yaw rate γ, that is, lateral slip acceleration $V_{Yd}$ of the vehicle is calculated. The lateral slip velocity $V_Y$ of the vehicle may be calculated by integrating the lateral slip acceleration $V_{Yd}$, and the slip angle $\beta_B$ of the vehicle may be calculated as a ratio of the lateral slip velocity $V_Y$ to the longitudinal speed $V_X$ of the vehicle (=vehicle speed V), that is, a ratio $V_Y/V_X$.

9. Calculation of the Corrected Wheel Speed

The wheel speed $VW_i$ of each wheel is converted into the longitudinal speed at the center of gravity 104 of the vehicle (hereinafter, referred to as "corrected vehicle speed $SVW_i$" (i=fl, fr, rl, rr)).

Figure 6:
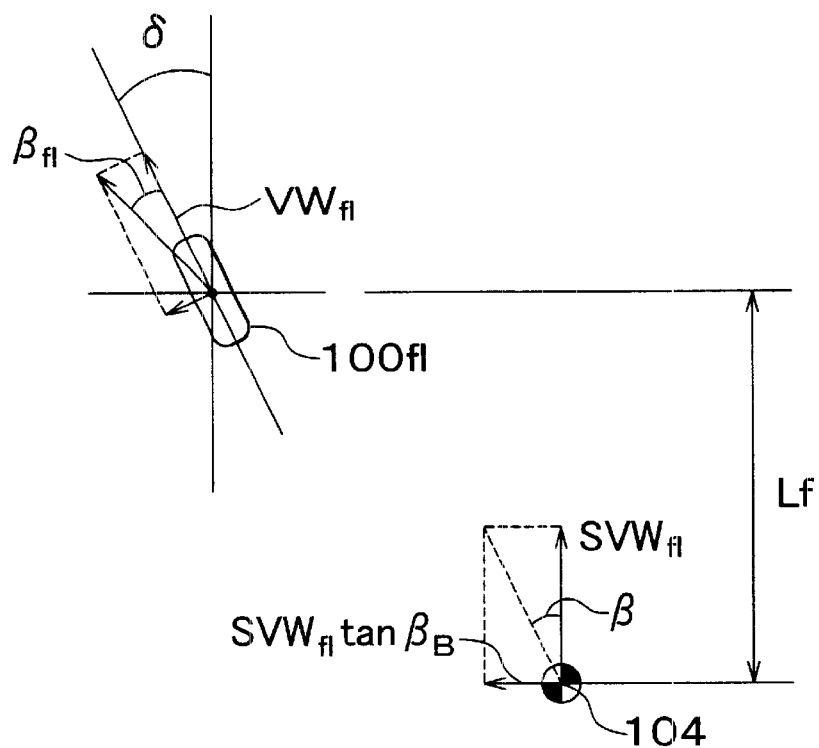
FIG. 6 is a diagram illustrating a method for calculating a corrected vehicle speed $SVW_i$ based on a wheel speed $VW_i$ of each wheel.

For example, as shown in FIG. 6, the following equations (109) and (110) are obtained for the left front wheel:

$$\frac{VW_{fl}}{\cos\beta_f}\cos(\delta + \beta_f) = SVW_{fl} - \frac{Tr}{2}\gamma \quad (109)$$

$$\frac{VW_{fl}}{\cos\beta_f}\sin(\delta + \beta_f) = SVW_{fl}\tan\beta_B + L_f\gamma. \quad (110)$$

Based on the above equations (109) and (110), the corrected wheel speeds $SVW_{fl}$, $SVW_{fr}$ of the left and right front wheels are respectively obtained by the following equations (111) and (112):

$$SVW_{fl} = \frac{-\left(-\frac{Tr}{2} + L_f\tan\beta_B\right)\gamma + \sqrt{(1+\tan^2\beta_B)\left(\frac{VW_{fl}}{\cos\beta_f}\right)^2 - \left(L_f + \frac{Tr}{2}\tan\beta_B\right)^2\gamma^2}}{1+\tan^2\beta_B} \quad (111)$$

$$SVW_{fr} = \frac{-\left(-\frac{Tr}{2} + L_f\tan\beta_B\right)\gamma + \sqrt{(1+\tan^2\beta_B)\left(\frac{VW_{fr}}{\cos\beta_f}\right)^2 - \left(L_f - \frac{Tr}{2}\tan\beta_B\right)^2\gamma^2}}{1+\tan^2\beta_B}. \quad (112)$$

The corrected wheel speeds $SVW_{rl}$, $SVW_{rr}$ of the left and right rear wheels are respectively obtained by the following equations (113) and (114):

$$SVW_{rl} = VW_{rl} + \frac{Tr}{2}\gamma \quad (113)$$

$$SVW_{rr} = VW_{rr} - \frac{Tr}{2}\gamma. \quad (114)$$

10. Calculation of the Estimated Vehicle Speed and the Slip Ratio of Each Wheel (1) Reference Slip Ratio SK The slip ratio for calculating the estimated vehicle speed VB (hereinafter, referred to as "reference slip ratio SK") is defined as follows:

When $|F_X|$ is large and $|F_Y|$ is large:

The reference slip ratio SK is given by the following equation (115), based on the above equations (98) and (103) of the tire model:

$$SK = \frac{\frac{K_\beta}{K_S}\tan\beta}{\frac{F_Y}{F_X} - \frac{K_\beta}{K_s}\tan\beta}. \tag{115}$$

When $|F_X|$ is large and $|F_Y|$ is small:

From the above equation (82) of the tire model (where $\beta=0$), the reference slip ratio SK is given by the following equation (120) based on the following equations (116) to (119):

$$\lambda = |S| \tag{116}$$

$$\xi = 1 - \frac{K_S}{3\mu_{max}F}|S| \tag{117}$$

$$F_{XY} = \mu_{max}F_Z(1-\xi^3) \tag{118}$$

$$|F_X| = F_{XY} \tag{119}$$

$$|SK| = \left(1 - \sqrt[3]{1 - \frac{|F_X|}{\mu_{max}F_Z}}\right)\frac{3\mu_{max}F_Z}{K_S}. \tag{120}$$

When $|F_X|$ is small

In this case, the reference slip ratio SK is zero. The reference slip ratio SK is thus given by the following equation (121):

$$SK = 0 \tag{121}.$$

Accordingly, the reference slip ratio SK (the reference slip ratio $SK_i$ of each wheel (i=fl, fr, rl, rr)) is calculated by substituting for the above equations (115) and (120) the longitudinal force $F_X$ and the like calculated in the sections 2 to 5, 7 and 8 above and the section 11 below.

(2) Estimated Vehicle Speed

Based on the largest value among the corrected wheel speeds $SVW_i$ calculated in the section 9 above and the reference slip $SK_i$ of that wheel, the estimated vehicle speed VB is calculated according to the following equation (122). The reason why the largest value among the corrected wheel speeds $SVW_i$ is used is because this value is the closest to the actual vehicle speed.

$$VB = SVW_i(1+SK_i) \tag{122}$$

(3) Slip Ratio of Each Wheel

The slip ratio $S_i$ of each wheel (i=fl, fr, rl, rr) is calculated according to the following equations (123) to (126), based on the estimated vehicle speed VB and the reference slip ratio $SK_i$ of each wheel:

$$S_{fl} = \frac{VB - SVW_{fl}}{SVW_{fl}} \tag{123}$$

$$S_{fr} = \frac{VB - SVW_{fr}}{SVW_{fr}} \tag{124}$$

$$S_{rl} = \frac{VB - SVW_{rl}}{SVW_{rl}} \tag{125}$$

$$S_{rr} = \frac{VB - SVW_{rr}}{SVW_{rr}}. \tag{126}$$

11. Calculation of the Maximum Road Friction Coefficient of Each Wheel

Based on the vertical load $F_Z$ in the section 2 above, the reaction force of the road to the tire $F_{XY}$ in the section 5 above, and the above equations (99) and (104) of the tire model, the maximum road friction coefficient $\mu_{max}$ is given by the following equation (127). Note that, in the equation (127), $\Delta\mu$ is a positive constant, and $(\partial F_{XY}/\partial\lambda)_{\lambda=0}$ is the value $(\partial F_{XY}/\partial\lambda)$ when $\lambda=0$.

$$\mu_{max} = \frac{F_{XY}}{F_Z} + \Delta\mu \frac{\frac{1}{F_Z}\frac{\partial F_{XY}}{\partial\lambda}}{\frac{1}{F_Z}\left(\frac{\partial F_{XY}}{\partial\lambda}\right)_{\lambda=0}} = \frac{F_{XY}}{F_Z} + \Delta\mu \frac{\frac{\partial F_{XY}}{\partial\lambda}}{\left(\frac{\partial F_{XY}}{\partial\lambda}\right)_{\lambda=0}} \tag{127}$$

Figure 7:
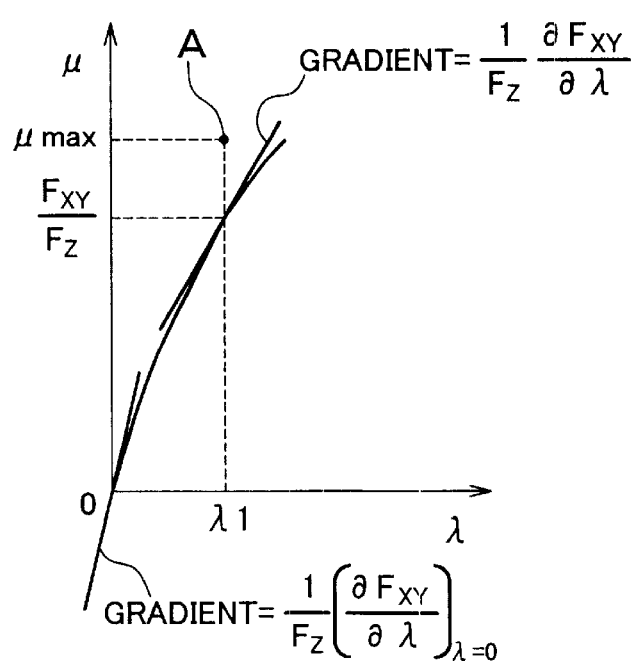
FIG. 7 is a graph illustrating the gradient $(1/F_Z)(\partial F_{XY}/\partial \lambda)$ in the $\mu$–$\lambda$ curve.

As shown in FIG. 7, $(1/F_Z)(\partial F_{XY}/\partial\lambda)_{\lambda=0}$ is an inclination of the $\mu$-$\lambda$ curve at the origin. $(1/F_Z)(\partial F_{XY}/\partial\lambda)$ is an inclination of the $\mu$-$\lambda$ curve for a specific value $\lambda$ (e.g., $\lambda 1$). As shown in FIG. 3B, the inclination of the $\mu$-$\lambda$ curve gradually decreases as the composite slip ratio $\lambda$ increases. In the region of the maximum road friction coefficient $\mu_{max}$, the inclination of the $\mu$-$\lambda$ curve is zero regardless of the composite slip ratio $\lambda$.

Accordingly, provided that the minimum value of the composite slip ratio $\lambda$ in the region of the maximum road friction coefficient $\mu_{max}$ is $\lambda e$, the ratio between the inclinations of the $\mu$-$\lambda$ curve in the second term of the above equation (127) gradually decreases in the region of $\lambda<\lambda e$ as the composite slip ratio $\lambda$ increases. In the region of $\lambda\geq\lambda e$, this ratio is zero. According to the above equation (127), the maximum friction coefficient $\mu_{max}$ in the region of $\lambda<\lambda e$ is estimated to be a value that is higher than the value $F_{XY}/F_Z$ by the value of the product of $\Delta\mu$ and the aforementioned ratio between the inclinations. In the region of $\lambda>\lambda e$, the maximum friction coefficient $\mu_{max}$ is estimated to be a true maximum friction coefficient.

Figure 8:
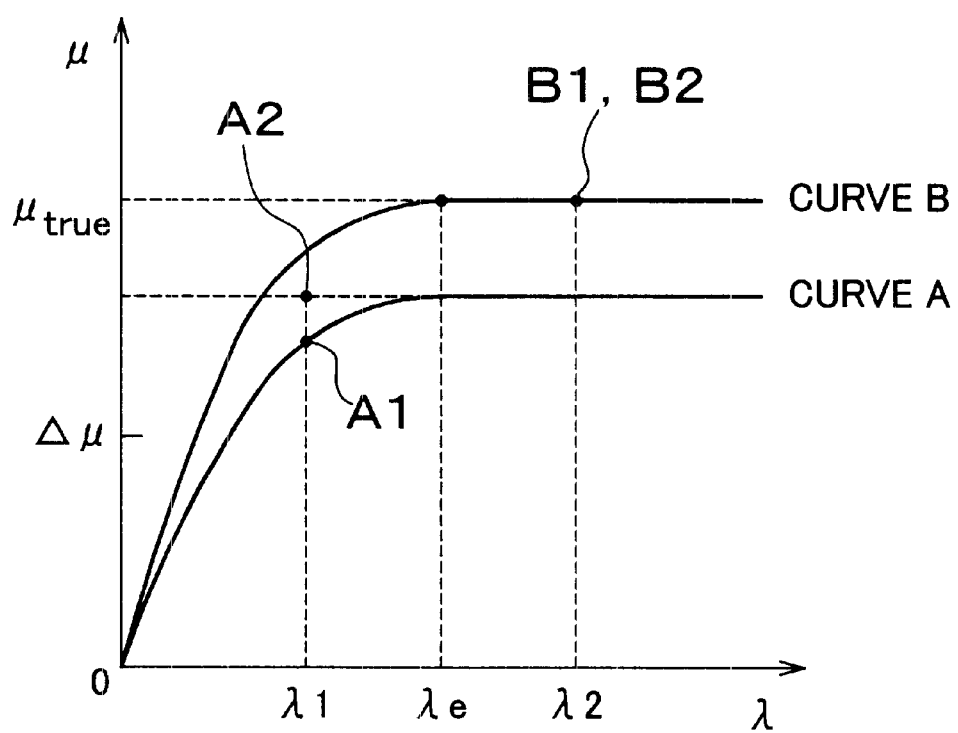
FIG. 8 is a graph of the $\mu$–$\lambda$ curve illustrating a method for calculating the maximum road friction coefficient $\mu_{max}$.

For example, as shown in FIG. 8, it is herein assumed that the true maximum friction coefficient is $\mu_{true}$, and the value $F_{XY}/F_Z$ corresponds to the point A1 when the value $\lambda$ is equal to $\lambda 1$ ($\lambda 1 < \lambda e$). In this case, the maximum friction coefficient $\lambda_{max}$ is estimated to be a value corresponding to the point A2, whereby the $\mu$-$\lambda$ curve is estimated as curve A. In contrast, provided that the value $F_{XY}/F_Z$ corresponds to the point B1 when $\lambda$ is equal to $\lambda 2$ ($\lambda 2 \geq \lambda e$), the maximum friction coefficient $\mu_{max}$ is estimated to be a value corresponding to the same point B2 as the point B1, whereby the $\mu$-$\lambda$ curve is estimated as curve B.

As can be seen from FIG. 8, the estimation error of the maximum friction coefficient $\mu_{max}$ is increased when $\lambda$ is small. When the constant $\Delta\mu$ is set to a small value, the maximum friction coefficient $\mu_{max}$ is estimated to be a value smaller than the true maximum friction coefficient $\mu_{true}$. In contrast, when the constant $\Delta\mu$ is set to a large value, the maximum friction coefficient $\mu_{max}$ is estimated to be a value larger than the true maximum friction coefficient $\mu_{true}$. However, the estimation error of the maximum friction coefficient gradually decreases as $\lambda$ increases. In the region of $\lambda\geq\lambda e$, the maximum friction coefficient $\mu_{max}$ is correctly estimated to be the true maximum friction coefficient $\mu_{true}$.

Note that, according to the equation (83) of the tire model, $\xi$ is equal to 1 when the composite slip ratio $\lambda$ is zero. In this case, the following equation (128) is obtained:

$$\left(\frac{\partial F_{XY}}{\partial \lambda}\right)_{\lambda=0} = K_S. \quad (128)$$

As described above in the section 6, a current maximum friction coefficient $\mu_{max}$ is required to calculate $\partial F_{XY}/\partial \lambda$. Accordingly, $\partial F_{XY}\cdot\partial\lambda$ is calculated by using the previous calculated value $\mu_{max(n-1)}$ as the maximum friction coefficient $\mu_{max}$. Based on the calculated value $\partial F_{XY}/\partial \lambda$, the maximum friction coefficient $\mu_{max}$ is calculated according to the above equation (127).

Hereinafter, a first embodiment of the invention will be described in detail in conjunction with the accompanying drawings.

Figure 9:
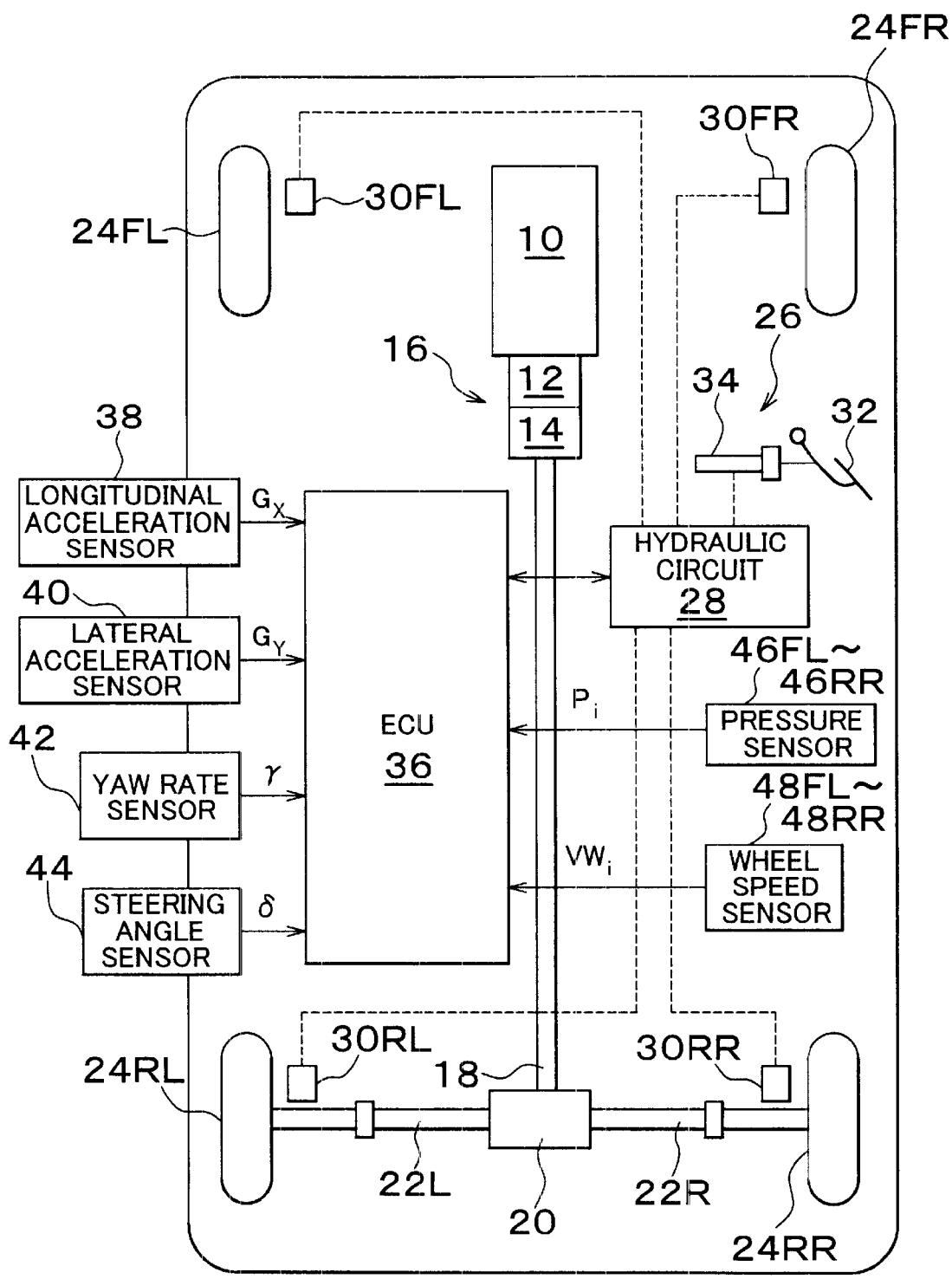
FIG. 9 is a schematic structural diagram showing a maximum friction coefficient estimating apparatus applied to a rear-wheel-drive vehicle, according to a first embodiment of the invention.

FIG. 9 is a schematic structural diagram showing a maximum friction coefficient estimating apparatus applied to a rear-wheel-drive vehicle, according to the first embodiment of the invention.

In FIG. 9, reference numeral 10 denotes an engine. The driving force of the engine 10 is transmitted to a propeller shaft 18 through an automatic transmission 16 that includes a torque converter 12 and a transmission 14. The driving force of the propeller shaft 18 is transmitted to a left rear axle 22L and a right rear axle 22R through a differential 20. Left and right rear wheels 24RL and 24RR serving as driving wheels are thus rotated.

Left and right front wheels 24FL and 24FR serve as driven wheels as well as steering wheels. Although not shown in FIG. 9, the front wheels 24FL and 24FR are steered through a tie rod by a rack-and-pinion type power steering device that is driven in response to turning of the steering wheel by the driver.

The braking force of the left and right front wheels 24FL, 24FR and the left and right rear wheels 24RL, 24RR is controlled by controlling the braking pressure of corresponding wheel cylinders 30FL, 30FR, 30RL, 30RR by a hydraulic circuit 28 in a brake system 26. Although not shown in FIG. 9, the hydraulic circuit 28 includes an oil reservoir, an oil pump, various valve devices and the like. The braking pressure of each wheel cylinder is normally controlled by an electronic control unit (ECU) 36 according to the pressure in a mask cylinder 34 that is driven in response to a depressing operation of a brake pedal 32 by the driver. The control pressure of each wheel cylinder is controlled by the ECU 36 so as to stabilize the vehicle's behavior as required.

The ECU 36 receives the following signals: a signal indicating longitudinal acceleration $G_X$ of the vehicle detected by a longitudinal acceleration sensor 38; a signal indicating lateral acceleration $G_Y$ of the vehicle detected by a lateral acceleration sensor 40; a signal indicating a yaw rate $\gamma$ of the vehicle detected by a yaw rate sensor 42; a signal indicating a steering angle $\delta$ detected by a steering angle sensor 44; a signal indicating a pressure $P_i$ (i=fl, fr, rl, rr) in the wheel cylinders 30FL to 30RR of the left and right front wheels and the left and right rear wheels detected by pressure sensors 46FL to 46RR; and a signal indicating a wheel speed $VW_i$ (i=fl, fr, rl, rr) of the left and right front wheels and the left and right rear wheels detected by vehicle speed sensors 48FL to 48RR.

Note that the ECU 36 actually includes a CPU (central processing unit), a ROM (read only memory), a RAM (random access memory), and an input/output (I/O) port device. The ECU 36 may be formed from a microcomputer of a well-known structure having these elements connected together through a bi-directional common bus, and a driving circuit.

Figure 10:
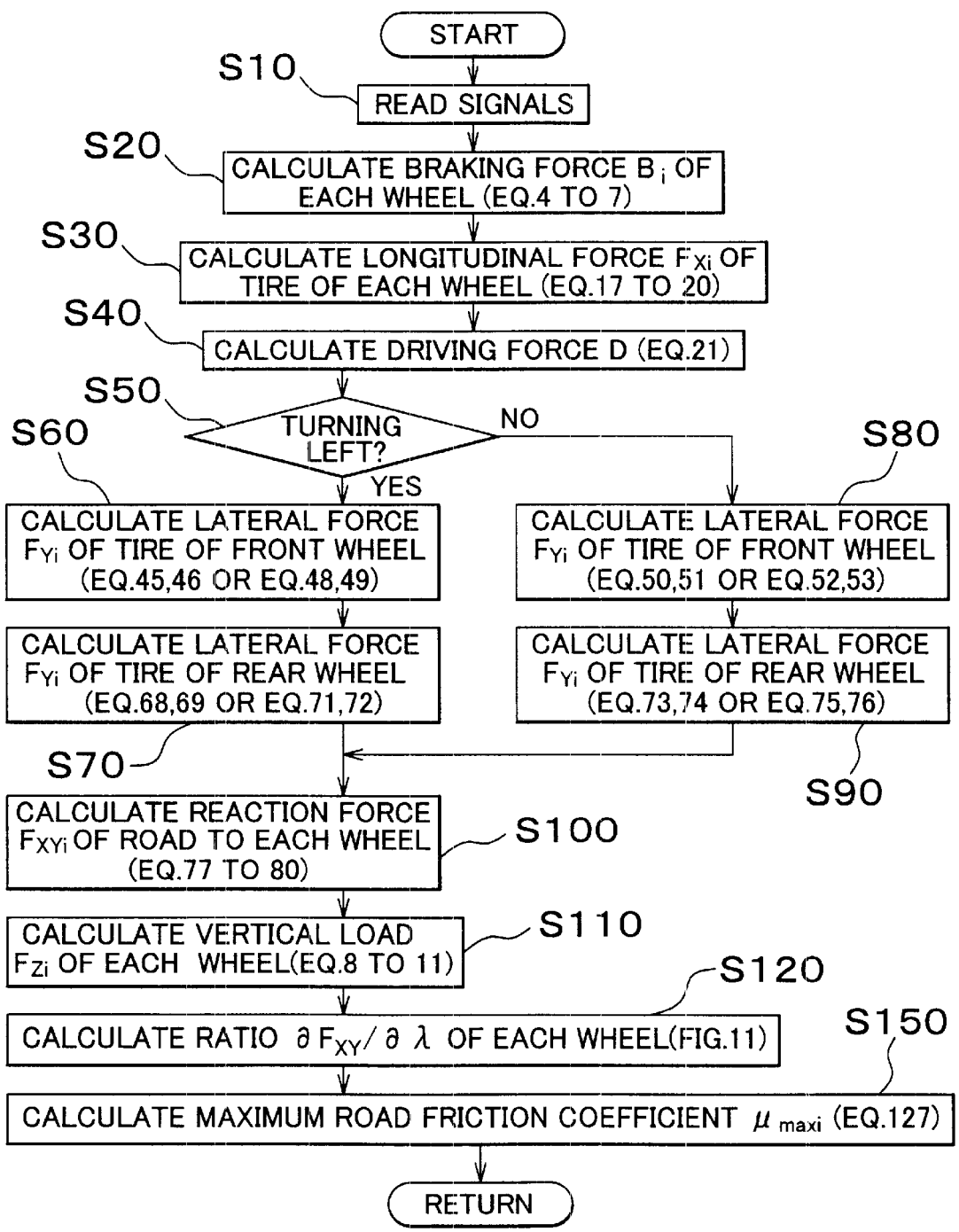
FIG. 10 is a flowchart illustrating a routine for estimating the maximum friction coefficient according to the first embodiment.
Figure 11:
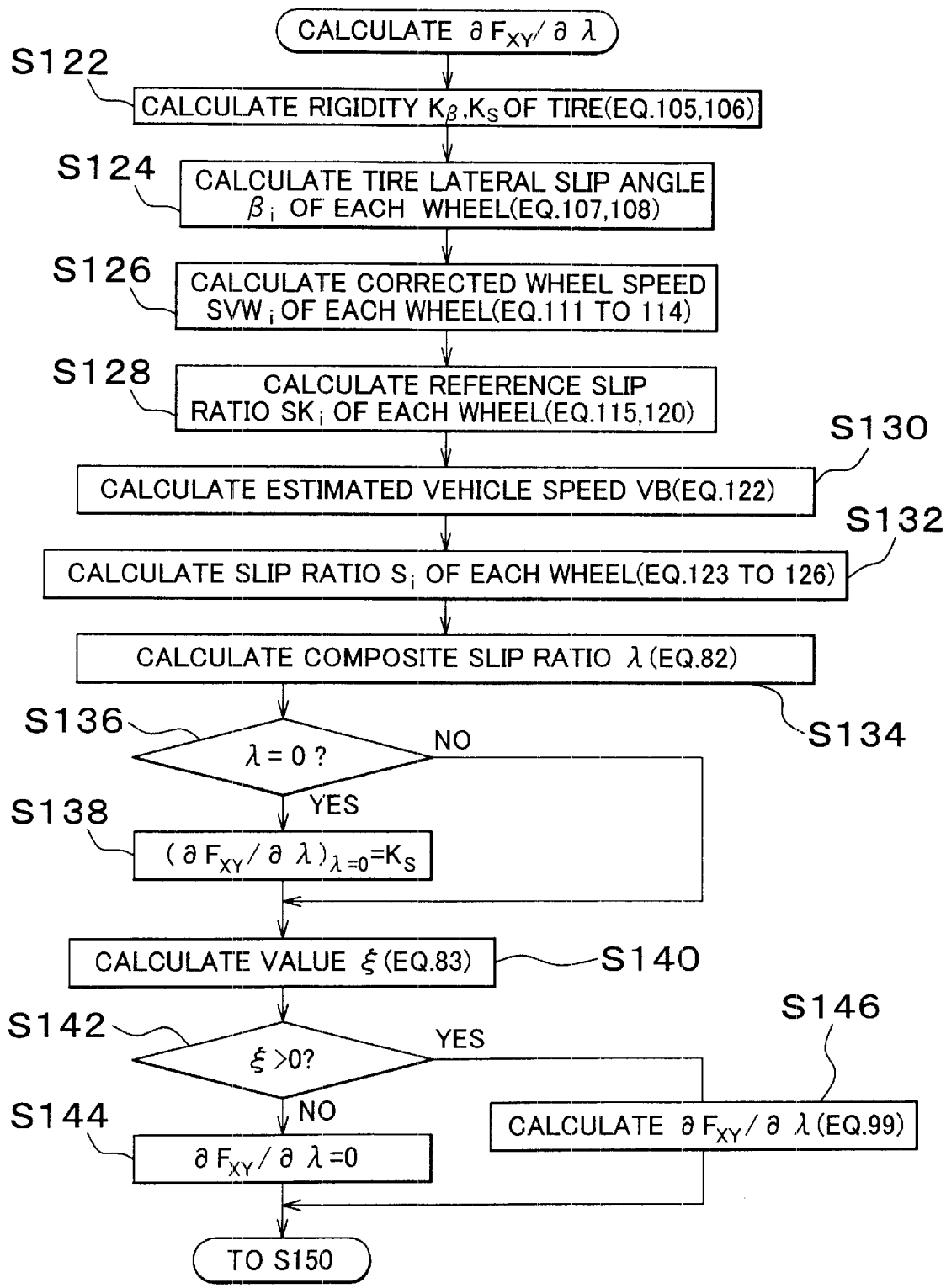
FIG. 11 is a flowchart illustrating a subroutine for calculating the ratio $\partial F_{XY}/\partial \lambda$ in Step S120 of FIG. 10.

The ECU 36 stores the control flows of FIGS. 10 and 11. The ECU 36 calculates the following values: the longitudinal force $F_{Xi}$ and lateral force $F_{Yi}$ of the tire of each wheel described below (i=fl, fr, rl, rr); the reaction force $F_{XYi}$ of the road to each wheel (i=fl, fr, rl, rr) based on the longitudinal and lateral forces $F_{xi}$ and $F_{Yi}$ of the tire; the vertical load $F_{Zi}$ of each wheel (i=fl, fr, rl, rr); and the ratio of variation in reaction force $F_{XY}$ to variation in composite slip ratio $\lambda$ for each wheel, $\partial F_{XY}/\partial \lambda$. Based on these values, the ECU 36 calculates the maximum friction coefficient $\mu_{max}$ for each wheel.

Although not shown in the figure, the ECU 36 calculates the values such as yaw moment $M_i$ around the center of gravity of the vehicle resulting from the reaction force $F_{XYi}$ of the road (i=fl, fr, rl, rr), and determines the vehicle's behavior based on the calculated yaw moment $M_i$ and the like. When the vehicle is in a spin state or in a drift-out state, the ECU 36 controls the braking pressure on a predetermined wheel to apply required braking force to the predetermined wheel, thereby stabilizing the vehicle's behavior. Note that, since control of the vehicle's behavior based on the yaw moment $M_i$ and the like does not form a subject matter of the invention, detailed description thereof is omitted.

Hereinafter, a routine for calculating the maximum friction coefficient according to the first embodiment will be described with reference to the flowcharts of FIGS. 10 and 11. Note that control according to the flowcharts of FIGS. 10 and 11 is started in response to closing of an ignition switch, not shown, and is repeated at predetermined intervals of time.

First, in Step S10, signals such as a signal indicating the longitudinal acceleration $G_X$ of the vehicle detected by the longitudinal acceleration sensor 38 are read. In Step S20, the braking force $B_i$ of each wheel is calculated according to the above equations (4) to (7), based on the braking pressure $P_i$.

In Step S30, the wheel acceleration $VWd_i$ is calculated as a time derivative value of the wheel speed $VW_i$, and the longitudinal tire force $F_{Xi}$ of each wheel is calculated according to the above equations (17) to (20), based on the wheel acceleration $VWd_i$ and the like. In Step S40, the driving force D of the vehicle is calculated according to the above equation (21).

In Step S50, whether the vehicle is turning to the left or not is determined based on, e.g., the sign of the yaw rate $\gamma$ of the vehicle detected by the yaw rate sensor 42. If NO in Step S50, the routine proceeds to Step S80. If YES in Step S50, the routine proceeds to Step S60. Note that determination of the turning state of the vehicle may be conducted by any method that is known in the art.

In Step S60, the lateral forces of the tires of the left and right front wheels, $F_{Yfl}$ and $F_{Yfr}$, are calculated according to the above equations (45) and (46) or equations (48) and (49), respectively. In Step S70, the lateral forces of the tires of the left and right rear wheels, $F_{Yrl}$ and $F_{Yrr}$, are calculated according to the above equations (68) and (69) or equations (71) and (72), respectively.

Similarly, in Step S80, the lateral forces of the tire of the left and right front wheels, $F_{Yfl}$ and $F_{Yfr}$, are calculated according to the above equations (50) and (51) or equations (52) and (53), respectively. In Step S90, the lateral forces of the tires of the left and right rear wheels, $F_{Yrl}$ and $F_{Yrr}$, are calculated according to the above equations (73) and (74) or equations (75) and (76), respectively.

In Step S100, the reaction force of the road to each wheel, $F_{XYi}$, is calculated according to the above equations (77) to (80), based on the longitudinal and lateral forces $F_{Xi}$ and $F_{Yi}$ of the tire of each wheel. In Step S110, the vertical load of each wheel, $F_{Zi}$, is calculated according to the above equations (8) and (11), based on the longitudinal acceleration $G_X$ of the vehicle and the like.

In Step S120, the ratio of variation in reaction force of the road $F_{XY}$ to variation in composite slip ratio $\lambda$, that is, the ratio $\partial F_{XY}/\partial \lambda$, is calculated for each wheel according to the routine of FIG. 11. In Step S150, the maximum road friction coefficient $\mu_{maxi}$ is calculated for each wheel according to the above equation (127). The routine then returns to Step S10.

In Step S122 of the routine for calculating the ratio $\partial F_{XY}/\partial \lambda$ in Step S120 of FIG. 10, the longitudinal rigidity $K_S$ and lateral tire rigidity $K_\beta$ of the tire is calculated for each wheel according to the above equations (105) and (106). In Step S124, the lateral slip angle $\beta_B$ of the vehicle is calculated by a method known in the art, and based on the calculated lateral slip angle $\beta_B$, the lateral slip angle $\beta_i$ of each wheel is calculated according to the above equations (107) and (108).

In Step S126, the corrected vehicle speed $SVW_i$ of each wheel is calculated according to the above equations (111) to (114). In Step S128, the reference slip ratio $SK_i$ of each wheel is calculated according to the above equation (115) or (120). In Step S130, the estimated vehicle speed VB is calculated according to the above equation (122), based on the largest value among the corrected wheel speeds $SVW_i$.

In Step S132, the slip ratio $S_i$ of each wheel is calculated according to the above equations (123) to (126), based on the estimated vehicle speed VB and the reference slip ratio $SK_i$ of each wheel. In Step S134, the composite slip ratio $\lambda$ is calculated according to the above equation (82).

In Step S136, whether the composite slip ratio $\lambda$ is equal to zero or not is determined. If NO in Step S136, the routine proceeds to Step S140. If YES in Step S136, the routine proceeds to Step S138. In Step S138, the ratio $\partial F_{XY}/\partial \lambda$, (the ratio of variation in reaction force of the road, $F_{XY}$, to variation in composite slip ratio $\lambda$) for $\lambda=0$, that is, the ratio $(\partial F_{XY}/\partial \lambda)_{\lambda=0}$, is set to the vertical rigidity $K_S$ of the tire. The routine then proceeds to Step S140.

In Step S140, the value $\xi$ is calculated according to the above equation (83), based on the previous calculated value of the maximum friction coefficient $\mu_{max}$ and the like. In Step S142, whether the value $\xi$ is positive or not is determined. If NO in Step S142, the routine proceeds to Step S144, where the ratio $\partial F_{XY}/\partial \lambda$ (the ratio of variation in reaction force of the road, $F_{XY}$, to variation in composite slip ratio $\lambda$) is set to zero. If YES in Step S142, the routine proceeds to Step S146, where the ratio $\partial F_{XY}/\partial \lambda$ is calculated according to the above equation (99), based on the previous calculated value of the maximum friction coefficient $\mu_{max}$ and the like.

Although not specifically shown in FIG. 11, Steps S134 to S146 are sequentially conducted on a wheel-by-wheel basis in the order of, e.g., the left front wheel, right front wheel, left rear wheel and right rear wheel. Accordingly, the composite slip ratio X and the like are calculated for each wheel.

According to the first embodiment, the braking force $B_i$ of each wheel is calculated in Step S20. The longitudinal force $F_{Xi}$ of the tire of each wheel is calculated in Step S30. The driving force D of the vehicle is calculated in Step S40. The lateral force $F_{Yi}$ of the tire of each wheel is calculated in Steps S50 to S90. The reaction force of the road to each wheel, $F_{XYi}$, is calculated in Step S100. The vertical load $F_{Zi}$ of each wheel is calculated in Step S110.

In Step S120, the ratio $\partial F_{XY}/\partial \lambda$ (the ratio of variation in reaction force of the road, $F_{XY}$, to variation in composite slip ratio $\lambda$) is calculated for each wheel. In Step S150, the maximum road friction coefficient $\mu_{maxi}$ is calculated for each wheel according to the equation (127) as the sum of the ratio $F_{XYi}/F_{Zi}$ (the ratio of the reaction force of the road, $F_{XYi}$, to the vertical load $F_{Zi}$) and the product of a predetermined coefficient and the ratio $\partial F_{XY}/\partial \lambda$.

According to the first embodiment, as described above in the section 11, an estimated maximum friction coefficient gradually gets closer to the actual maximum friction coefficient as the composite slip ratio increases. Accordingly, in the region of the high composite slip ratio, the maximum road friction coefficient $\mu_{maxi}$ can be accurately estimated on a wheel-by-wheel basis.

Note that, in the region of the low composite slip ratio, the maximum road friction coefficient cannot be estimated accurately. However, information on the maximum road friction coefficient is generally required when behavior control for stabilizing deteriorated behavior of the vehicle is to be conducted. The composite slip ratio is high in such a situation. Therefore, according to the first embodiment, the maximum road friction coefficient can be accurately estimated in the situation where the information on the maximum road friction coefficient is required. This enables accurate behavior control. Moreover, such low estimation accuracy of the maximum road friction coefficient in the region of the low composite slip ratio will not cause any excessive inconveniences.

According to the first embodiment, estimation can be conducted even when the wheels are not in a predetermined acceleration slip state. Therefore, the maximum road friction coefficient can be accurately estimated much more frequently than in the case of the aforementioned conventional estimating apparatus. The maximum road friction coefficient can also be estimated accurately for the driven wheels.

Second Embodiment

Figure 12:
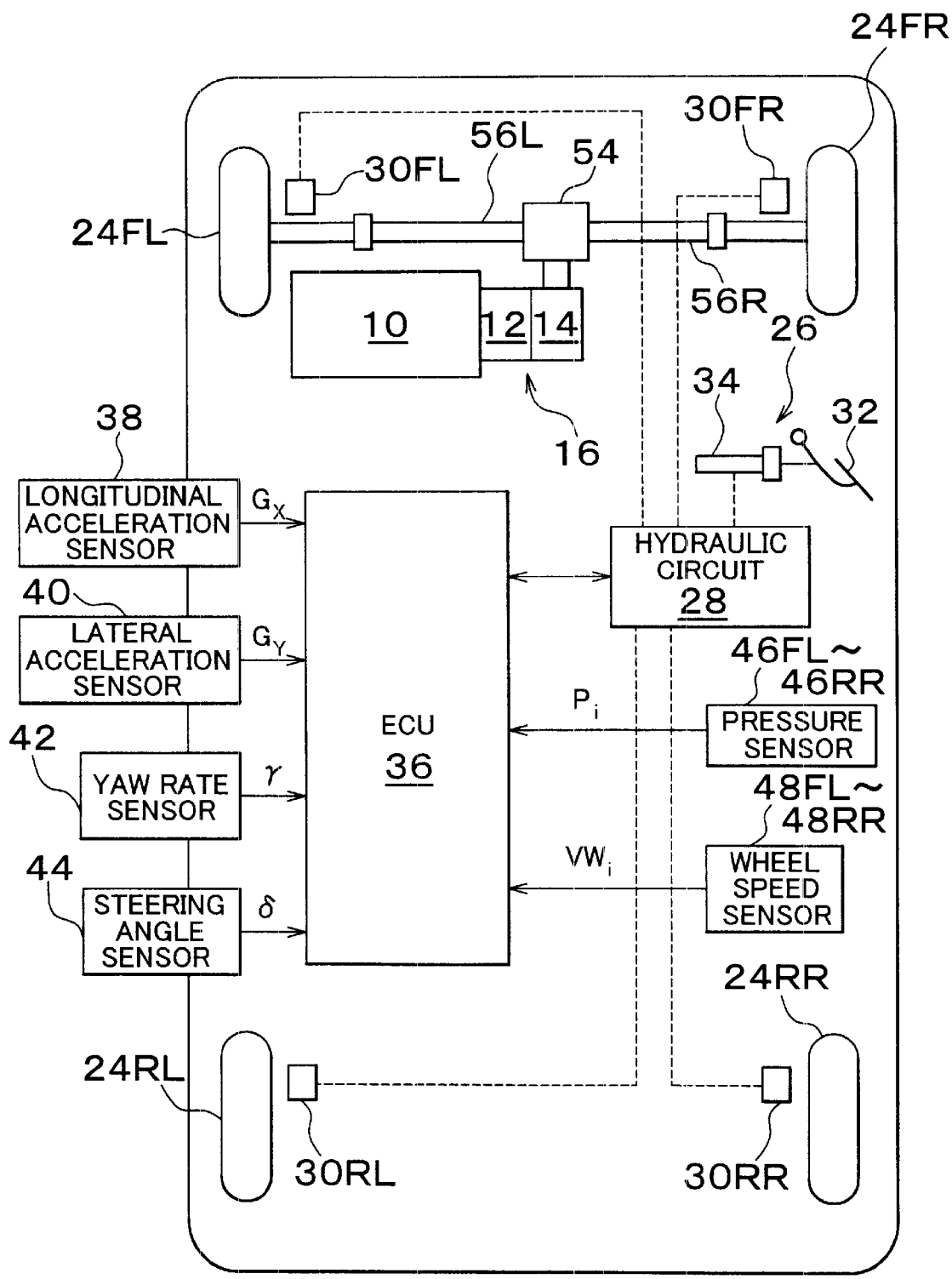
FIG. 12 is a schematic structural diagram showing a maximum friction coefficient estimating apparatus applied to a front-wheel-drive vehicle, according to a second embodiment of the invention.

FIG. 12 is a schematic structural diagram showing a maximum friction coefficient estimating apparatus applied to a front-wheel-drive vehicle, according to the second embodiment of the invention. FIG. 13 is a flowchart corresponding to FIG. 10, illustrating a routine for estimating the maximum friction coefficient according to the second embodiment. Note that the same members are denoted with the same reference numerals and characters in FIGS. 9 and 12, and the corresponding steps are denoted with the same step numbers in FIGS. 10 and 13.

In the second embodiment, the driving force of the engine 10 is transmitted to a left front axle 56L and a right front axle 56R through the automatic transmission 16 and a differential 54. Thus, the left and right front wheels 24FL and 24FR serving as steering wheels as well as driving wheels are rotated.

In the second embodiment, the longitudinal force $F_{Xi}$ of the tire of each wheel is calculated in Step S30 according to the above equations (26) to (29). In Step S40, the driving force D of the vehicle is calculated according to the above equation (30). In other respects, the maximum road friction coefficient $\mu_{max}$ of each wheel is calculated in the same manner as that of the first embodiment.

According to the second embodiment, the maximum road friction coefficient $\mu_{maxi}$ can be accurately estimated on a wheel-by-wheel basis in the region of the high composite slip ratio even when the vehicle is a front-wheel-drive vehicle. Moreover, as in the first embodiment, the maximum road friction coefficient can be accurately estimated much more frequently than in the case of the aforementioned conventional estimating apparatus. Accordingly, the maximum road friction coefficient can also be estimated accurately for the driven wheels.

In particular, according to the illustrated embodiments, a coefficient $\Delta\mu\cdot\{(\partial F_{XY}/\partial\lambda)\}_{\lambda=0}$ for the ratio $\partial F_{XY}/\partial\lambda$ (the ratio of variation in reaction force of the road, $F_{XY}$ to variation in composite slip ratio $\lambda$) is inversely proportional to the ratio $\partial F_{XY}/\partial\lambda$ for $\lambda=0$, that is, $(\partial F_{XY}/\partial\lambda)_{\lambda=0}$. Accordingly, the maximum road friction coefficient $\mu_{maxi}$ can be more accurately estimated for each wheel as compared to the case where this coefficient is constant.

The specific embodiments of the invention have been described in detail. However, it should be appreciated by those skilled in the art that the invention is not limited to the above embodiments, and various other embodiments are possible without departing from the scope of the invention.

For example, the invention is applied to a rear-wheel-drive vehicle in the first embodiment, and applied to a front-wheel-drive vehicle in the second embodiment. However, the invention may be applied to a four-wheel drive vehicle. In this case, the longitudinal forces of the tires of the left and right front wheels, $F_{Xfl}$ and $F_{Xfr}$, and the longitudinal forces of the tires of the left and right rear wheels, $F_{Xrl}$, $F_{Xrr}$, are respectively calculated according to the following equations (129) to (132), based on the front-wheel distribution ratio $R_{df}$ and the rear-wheel distribution ratio $R_{dr}$ of the driving force applied from a four-wheel drive controller:

$$F_{Xfl} = B_{fl} + \frac{1}{2} D \cdot R_{df} - \frac{I_{wf} \cdot VWd_{fl}}{r^2} \quad (129)$$

$$F_{Xfr} = B_{fr} + \frac{1}{2} D \cdot R_{df} - \frac{I_{wf} \cdot VWd_{fr}}{r^2} \quad (130)$$

$$F_{Xrl} = B_{rl} + \frac{1}{2} D \cdot R_{df} - \frac{I_{wf} \cdot VWd_{rl}}{r^2} \quad (131)$$

$$F_{Xrr} = B_{rr} + \frac{1}{2} D \cdot R_{df} - \frac{I_{wf} \cdot VWd_{rr}}{r^2} \quad (132)$$

In the above embodiments, the coefficient $\Delta\mu\cdot\{(\partial F_{XY}/\partial\lambda)\}_{\lambda=0}$ for the ratio $\partial F_{XY}/\partial\lambda$ (the ratio of variation in reaction force of the road, $F_{XY}$, to variation in composite slip ratio $\lambda$) is set as a value inversely proportional to the ratio $\partial F_{XY}/\partial\lambda$ for $\lambda=0$, i.e., $(\partial F_{XY}/\partial\lambda)_{\lambda=0}$. However, this coefficient may be set to a fixed value.

In the above embodiments, the longitudinal rigidity $K_S$ and lateral rigidity $K_\beta$ of the tire are respectively calculated according to the above equations (105) and (106). However, these values may be calculated by another method. The longitudinal rigidity $K_S$ and lateral rigidity $K_\beta$ of the tire may be set to a constant.

As is apparent from the foregoing description, according to the invention, the maximum road friction coefficient can be calculated regardless of whether the wheel is in a predetermined drive slip state or not. Moreover, the maximum road friction coefficient can be calculated either for the driving wheels or driven wheels. Furthermore, the maximum road friction coefficient can be accurately calculated in the region of the high slip ratio.

In the illustrated embodiments, the controller is implemented with a general purpose processor. It will be appreciated by those skilled in the art that the controller can be implemented using a single special purpose integrated circuit (e.g., ASIC) having a main or central processor section for overall, system-level control, and separate sections dedicated to performing various different specific computations, functions and other processes under control of the central processor section. The controller can be a plurality of separate dedicated or programmable integrated or other electronic circuits or devices (e.g., hardwired electronic or logic circuits such as discrete element circuits, or programmable logic devices such as PLDs, PLAs, PALs or the like). The controller can be suitably programmed for use with a general purpose computer, e.g., a microprocessor, microcontroller or other processor device (CPU or MPU), either alone or in conjunction with one or more peripheral (e.g., integrated circuit) data and signal processing devices. In general, any device or assembly of devices on which a finite state machine capable of implementing the procedures described herein can be used as the controller. A distributed processing architecture can be used for maximum data/signal processing capability and speed.

While the invention has been described with reference to what are preferred embodiments thereof, it is to be understood that the invention is not limited to the preferred embodiments or constructions. To the contrary, the invention is intended to cover various modifications and equivalent arrangements. In addition, while the various elements of the preferred embodiments are shown in various combinations and configurations, which are exemplary, other combinations and configurations, including more, less or only a single element, are also within the spirit and scope of the invention.

What is claimed is:

1. A controller for determining a maximum friction coefficient between a tire of a wheel and a road, comprising:
    a first section that calculates a reaction force of the road to the tire of the wheel based on a tire model;
    a second section that calculates a vertical load of the tire of the wheel;
    a third section that calculates as a first ratio, a ratio of the reaction force of the road to the vertical load;
    a fourth section that calculates as a second ratio, a ratio of variation in the reaction force of the road to variation in a slip ratio of the tire, the slip ratio being calculated based on the tire model; and
    a fifth section that calculates a maximum road friction coefficient based on a product of a predetermined coefficient and the second ratio, and the first ratio.

2. The controller according to claim 1, wherein the fifth section calculates the maximum road friction coefficient by adding the first ratio to the product of the predetermined coefficient and the second ratio.

3. The controller according to claim 1, wherein the reaction force of the road is a reaction force in a two-dimensional plane on the road.

4. The controller according to claim 1, wherein the slip ratio is a composite slip ratio in a direction of the reaction force of the road.

5. The controller according to claim 1, wherein the first section further determines a longitudinal force and a lateral force of the tire of the wheel, and calculates the reaction force of the road to the tire of the wheel based on the longitudinal force and the lateral force of the tire.

6. The controller according to claim 5, wherein a series of calculations of the first to fifth sections is repeatedly conducted at predetermined intervals of time.

7. The controller according to claim 6, wherein the first section calculates the reaction force of the road to the tire of the wheel by using the longitudinal force of the tire of the wheel that is calculated based on a longitudinal acceleration of a vehicle, a steering angle, a braking force of the wheel, and a previous calculated value of the lateral force of the tire of the wheel.

8. The controller according to claim 5, wherein the first section calculates the reaction force of the road to the tire by using a lateral force of a tire of a front wheel that is calculated based on a yaw rate of a vehicle, a lateral acceleration of the vehicle, and the longitudinal force of the tire of the wheel.

9. The controller according to claim 5, wherein the first section calculates the reaction force of the road to the tire by using a lateral force of a tire of a rear wheel that is calculated based on a lateral acceleration of a vehicle, the longitudinal force of the tire of the wheel, and a lateral force of a tire of a front wheel.

10. A method for determining a maximum friction coefficient between a tire of a wheel and a road, comprising the steps of:

calculating a reaction force of the road to the tire of the wheel based on a tire model;

calculating a vertical load of the tire of the wheel;

calculating as a first ratio a ratio of the reaction force of the road to the vertical load;

calculating as a second ratio a ratio of variation in the reaction force of the road to variation in a slip ratio of the tire, the slip ratio being calculated based on the tire model; and calculating a maximum road friction coefficient based on a product of a predetermined coefficient and the second ratio, and the first ratio.

11. The method according to claim 10, wherein the maximum road friction coefficient is calculated by adding the first ratio to the product of the predetermined coefficient and the second ratio.

12. The method according to claim 10, wherein the reaction force of the road is a reaction force in a two-dimensional plane on the road.

13. The method according to claim 10, wherein the slip ratio is a composite slip ratio in a direction of the reaction force of the road.

14. The method according to claim 10, wherein the step of calculating the vertical load of the tire of the wheel includes the steps of estimating a longitudinal force and a lateral force of the tire of the wheel, and calculating the reaction force of the road to the tire of the wheel based on the longitudinal force and the lateral force of the tire.

15. The method according to claim 14, wherein a series of the steps in the method is repeatedly conducted at predetermined intervals of time.

16. The method according to claim 15, wherein the step of calculating the vertical load of the tire of the wheel includes the step of calculating the reaction force of the road to the tire of the wheel by using the longitudinal force of the tire of the wheel that is calculated based on a longitudinal acceleration of a vehicle, a steering angle, a braking force of the wheel, and a previous calculated value of the lateral force of the tire of the wheel.

17. The method according to claim 14, wherein the step of calculating the vertical load of the tire of the wheel includes the step of calculating the reaction force of the road to the tire by using a lateral force of a tire of a front wheel that is calculated based on a yaw rate of a vehicle, a lateral acceleration of the vehicle, and the longitudinal force of the tire of the wheel.

18. The method according to claim 14, wherein the step of calculating the vertical load of the tire of the wheel includes the step of calculating the reaction force of the road to the tire by using a lateral force of a tire of a rear wheel that is calculated based on a lateral acceleration of a vehicle, the longitudinal force of the tire of the wheel, and a lateral force of a tire of a front wheel.

19. A controller for determining a maximum friction coefficient between a tire of a wheel and a road, comprising:

a first section that calculates a reaction force of the road to the tire;

a second section that calculates a vertical load of the tire;

a third section that calculates variation in a slip ratio of the tire;

a fourth section that calculates variation in the reaction force of the road to the tire; and a fifth section that calculates a maximum road friction coefficient based on the reaction force of the road, the vertical load, the variation in the slip ratio, and the variation in the reaction force of the road.

* * * * *